US011020497B2

(12) United States Patent
Steinmetz et al.

(10) Patent No.: US 11,020,497 B2
(45) Date of Patent: Jun. 1, 2021

(54) ROD-SHAPED PLANT VIRUS NANOPARTICLES AS IMAGING AGENT PLATFORMS

(71) Applicant: CASE WESTERN RESERVE UNIVERSITY, Cleveland, OH (US)

(72) Inventors: Nicole Steinmetz, San Diego, CA (US); Michael Bruckman, Cleveland, OH (US)

(73) Assignee: CASE WESTERN RESERVE UNIVERSITY, Cleveland, OH (US)

(*) Notice: Subject to any disclaimer, the term of this patent is extended or adjusted under 35 U.S.C. 154(b) by 88 days.

(21) Appl. No.: 16/149,828

(22) Filed: Oct. 2, 2018

(65) Prior Publication Data

US 2019/0030193 A1  Jan. 31, 2019

Related U.S. Application Data

(63) Continuation of application No. 14/434,435, filed as application No. PCT/US2013/064136 on Oct. 9, 2013, now Pat. No. 10,086,095.

(60) Provisional application No. 61/711,492, filed on Oct. 9, 2012.

(51) Int. Cl.
*C12N 15/82* (2006.01)
*C07K 14/005* (2006.01)
*C07K 14/08* (2006.01)
*C12N 7/00* (2006.01)
*A61K 39/00* (2006.01)
*A61K 49/18* (2006.01)

(52) U.S. Cl.
CPC ...... *A61K 49/1896* (2013.01); *A61K 49/1884* (2013.01); *C12N 7/00* (2013.01); *C12N 2770/00031* (2013.01)

(58) Field of Classification Search
CPC .... C07K 14/005; C12N 15/8258; C12N 7/00; C12N 15/8257; C12N 15/8283
See application file for complete search history.

(56) References Cited

U.S. PATENT DOCUMENTS

| | | | |
|---|---|---|---|
| 4,938,949 | A | 7/1990 | Borch et al. |
| 5,342,770 | A | 8/1994 | Yamasaki |
| 5,736,146 | A | 4/1998 | Cohen et al. |
| 7,666,624 | B2 | 2/2010 | Brennan |
| 2005/0019270 | A1 | 1/2005 | Finlay et al. |
| 2007/0258889 | A1* | 11/2007 | Douglas ............ A61K 49/085 424/1.37 |
| 2007/0284545 | A1 | 12/2007 | Isacsson et al. |
| 2009/0041671 | A1 | 2/2009 | Young et al. |
| 2011/0104051 | A1 | 5/2011 | Francis et al. |

FOREIGN PATENT DOCUMENTS

| | | |
|---|---|---|
| JP | 2009524699 A | 7/2009 |
| WO | 97/14443 A1 | 4/1997 |
| WO | 01/18199 A1 | 3/2001 |
| WO | 2001/0026682 A2 | 4/2001 |
| WO | 2009/143465 A1 | 11/2009 |
| WO | 2012/078069 A1 | 6/2012 |
| WO | WO2012078069 * | 6/2012 |
| WO | 2013/181557 A1 | 12/2013 |
| WO | 2015/0039255 A1 | 3/2015 |
| WO | 2016/073972 A1 | 5/2016 |

OTHER PUBLICATIONS

Raymond et al., "Next generation, high relaxivity gadolinium MRI Agents", Bioconjugate Chem., 2005, 16:3-8.*
Office action for Japanese Patent Application No. 2017-524349, dated Jan. 31, 2020.
Miermont et al., "Cowpea Mosaic Virus Capsid: A promising Carrier for the Development of Carbohydrate Based Antitumor Vaccines", Chem. Eur. J., 2008, vol. 14, pp. 4939-4947.
Sheen et al., "Stimulating Antitumor Immunity with Nanoparticles", Wiley Interdiscip Rev Nanomed Nanobiotechnol, Oct. 2014, vol. 6, pp. 496-505.
Office action for Chinese Patent Application No. 201580063662.6, dated Mar. 4, 2020.
Office action for European Patent Application No. 15 857 504.3—1111, dated Mar. 18, 2020.
Yildiz et al., "Applications of viral nanoparticles in medicine", Current Opinion in Biotechnology, vol. 22, Issue 6, pp. 901-908.
Aljabali, et al., "CPMV-DOX Delivers", Molecular Pharmaceutics, 2013, 10, pp. 3-10.
Wen, et al., "Interior Engineering of a Viral Nanoparticle and its Tumor Homing Properties" Macromolecules, vol. 13, No. 12, Dec. 2012.
Agrawal, et al., "Differential Uptake of Chemically Modified Cowpea Mosaic Virus Nanoparticles in Macrophage Subpopulations Present in Inflammatory and Tumor Microenvironments", Biomacromolecules, vol. 13, No. 10, Oct. 2012.
Brennan, et al., "Cowpea Mosaic Virus as a Vaccine Carrier of Heterologous Antigens", Molecular Biotechnology, vol. 17, No. 1, Jan. 2001.
Gonzalez, et al., "Interaction of Cowpea Mosaic Virus (CPMV) Nanoparticles with Antigen Presenting Cells in Vitro and in Vivo", PLOS ONE, vol. 4, No. 11, Nov. 2009.

(Continued)

*Primary Examiner* — Barry A Chestnut
(74) *Attorney, Agent, or Firm* — Tarolli, Sundheim, Covell & Tummino LLP

(57) ABSTRACT

A rod-shaped plant virus having an interior surface and an exterior surface, and at least one imaging agent that is linked to the interior and/or exterior surface is described. The rod-shaped viruses can be combined into larger spherical nanoparticles. A rod-shaped plant virus or spherical nanoparticles including an imaging agent can be used in a method of generating an image of a tissue region of a subject such as a tumor or atherosclerotic tissue by administering the virus particle to the subject and generating an image of the tissue region of the subject to which the virus particle has been distributed.

4 Claims, 10 Drawing Sheets

(56) References Cited

OTHER PUBLICATIONS

Iizotte, et al., "Plant-derived viral-like nanoparticle immunotherapy suppress development of metastatic lung cancer", Journal of Immunology, vol. 194, Issue 1 Supplement, May 2015.
Patrick H. Lizotte, "Novel approaches to targeting innate immunity for cancer immunotherapy", Proquest Dissertations Publishing, May 2015.
European Search Report for Patent Application No. 15857504.3—1111/3215520, dated May 7, 2018.
Supplementary European Search Report for Patent Application No. 15857504.3—111/3215520, dated May 28, 2018.
International Search Report for Application No. PCT/US15/59675.
Plchova et al. Expression of Human papillomavirus 16 E7ggg oncoprotein on N- and C-terminus of Potato virus X coat protein in bacterial and plant cells. Protein Expression and Purification 77 (2011) 146-152.
Smyth etal. Treatment of rapidly growing K-BALB and CT26 mouse tumours using Semliki Forest virus and its derived vector. Gene Therapy (2005) 12, 147-159.
Rohrer et al. Comparison of Magnetic Properties of MRI Contrast Media Solutions at Different Magnetic Field Strengths. Investigative Radiology. 2005; 40(11): 715-724.
Bruckman MA "Development of a viral nanoparticle for biomedical applications", Abstracts of Papers, 244th ACS National Meeting & Exposition, Philadelphia, PA, United States, Aug. 19-23, 2012 (2012), AEI-12. American Chemical Society: Washington, D.C.
Raymond et al. (Next generation, high relaxivity gadolinium MRI agents. Bioconjug Chem. 2005; 16(1 ): 3-8.
Garimella et al., "Multivalent, High-Relaxivity MRI Contrast Agents Using Rigid Cysteine-Reactive Gadolinium complexes", J Am Chem Soc. Sep. 21, 2011, 133(37), pp. 14704-14709.
Raymond et al., "Next Generation, High Relaxivity Gadolinium MRI Agents", Bioconjugate Chem. 2005, 16, pp. 3-8.
International Search Report for PCT/US2013/064136, dated Jan. 17, 2014, pp. 1-2.
Anderson et al., "Viral Nanoparticles Donning a Paramagnetic Coat: Conjugation of MRI Contrast Agents to the MS2 Capsid", Nano Letters, 2006, vol. 6, No. 6, pp. 1160-1164.
Janat-Amsbury et al. "Geometry and surface characteristics of gold nanoparticles influence their biodistribution and uptake by macrophages." European Journal of Pharmaceutics and Biopharmaceutics 77.3 (2011 ): 417-423.
Atabekov et al. "Thermal transition of native tobacco mosaic virus and RNA-free viral proteins into spherical nanoparticles." Journal of General Virology 92.2 (2011 ): 453-456.
Banci et al., "Nuclear and electron relaxation: the magnetic nucleus-unpaired electron coupling in solution". Wiley-VCH, 1991.
Boch ER, et al. "Synthesis of mono-and bifunctional peptide-dextran conjugates for the immobilization of peptide antigens on ELISA plates: properties and application." Journal of immunological methods 208.2 (1997): 191-202.
Boedtker et al., "The preparation and characterization of essentially uniform tobacco mosaic virus particles." Journal of the American Chemical Society 80.10 (1958): 2550-2556.
Bruckman et al., "Engineering Gd-loaded nanoparticles to enhance MRI sensitivity via T1 shortening." Nanotechnology 24.46 (2013): 462001.
Bruckman et al., "Surface modification of tobacco mosaic virus with "click" chemistry." ChemBioChem 9.4 (2008): 519-523.
Bruckman et al., "Tobacco mosaic virus rods and spheres as supramolecular high-relaxivity MRI contrast agents." Journal of Materials Chemistry B 1.10 (2013): 1482-1490.
Caravan et al., "Influence of molecular parameters and increasing magnetic field strength on relaxivity of gadolinium- and manganese-based T1 contrast agents." Contrast media & molecular imaging 4.2 (2009): 89-100.

Geng et al., "Shape effects of filaments versus spherical particles in flow and drug delivery." Nature nanotechnology 2.4 (2007): 249-255.
Gugliotta et al., "AAZTA-based bifunctional chelating agents for the synthesis of multimeric/dendrimeric MRI contrast agents." Organic & biomolecular chemistry 8.20 (2010): 4569-4574.
Hermanson, Greg T. Bioconjugate techniques. Academic press, 2013.
Hooker et al., "Magnetic resonance contrast agents from viral capsid shells: a comparison of exterior and interior cargo strategies." Nano letters 7.8 (2007): 2207-2210.
Huang et al., "Improving the magnetic resonance imaging contrast and detection methods with engineered magnetic nanoparticles." Theranostics 2.1 (2012): 86.
Klug "The tobacco mosaic virus particle: structure and assembly." Philosophical Transactions of the Royal Society B: Biological Sciences 354.1383 (1999): 531-535.
Lee et al., "Shape matters: the diffusion rates of TMV rods and CPMV icosahedrons in a spheroid model of extracellular matrix are distinct." Biomaterials science 1.6 (2013): 581-588.
Liepold et al., "Viral capsids as MRI contrast agents." Magnetic Resonance in Medicine 58.5 (2007): 871-879.
Lu et al., "Carboxylate interactions involved in the disassembly of tobacco mosaic tobamovirus." Virology 225.1 (1996): 11-20.
Nahrendorf, Matthias et al., "Noninvasive vascular cell adhesion molecule-1 imaging identifies inflammatory activation of cells in atherosclerosis." Circulation 114.14 (2006): 1504-1511.
Pokorski et al., "Functional virus-based polymer-protein nanoparticles by atom transfer radical polymerization." Journal of the American Chemical Society 133.24 (2011 ): 9242-9245.
Pokorski et al., "The art of engineering viral nanoparticles." Molecular pharmaceutics 8.1 (2010): 29-43.
Prasuhn et al., "Viral MRI contrast agents: coordination of Gd by native virions and attachment of Gd complexes by azide-alkyne cycloaddition." Chemical Communications 12 (2007): 1269-1271. 25.
Raymond et al., "Next generation, high relaxivity gadolinium MRI agents." Bioconjugate chemistry 16.1 (2005): 3-8.
Schlick et al., "Dual-surface modification of the tobacco mosaic virus." Journal of the American Chemical Society 127 .11 (2005): 3718-3723.
Shukla et al., "Increased tumor homing and tissue penetration of the filamentous plant viral nanoparticle Potato virus X." Molecular pharmaceutics 10.1 (2012): 33-42.
Steinmetz et al., "Intravital Imaging of Human Prostate Cancer Using Viral Nanoparticles Targeted to Gastrin-Releasing Peptide Receptors" Small 7.12 (2011): 1664-1672.
Tietze et al., "Conjugation of p-aminophenyl glycosides with squaric acid diester to a carrier protein and the use of the neoglycoprotein in the histochemical detection of lectins." Bioconjugate chemistry 2.3 (1991 ): 148-153.
Waters et al., "Contrast agents for MRI." Basic research in cardiology 103.2 (2008): 114-121.
Wen et al., "Design rules for nanomedical engineering: from physical virology to the applications of virus-based materials in medicine." Journal of biological physics 392 (2013): 301-325.
Wu et al., "Electrospinning fabrication, structural and mechanical characterization of rod-like virus-based composite nanofibers." Journal of Materials Chemistry 21.24 (2011 ): 8550-8557.
The Extended European Search Report for Application No. 13845276. 8, dated Apr. 18, 2016, pp. 1-8.
Steinmetz Nicole F. "Viral nanoparticles as platforms for next-generation therapeutics and imaging devices." Nanomedicine: Nanotechnology, Biology and Medicine 6.5 (2010): 634-641.

* cited by examiner

ROD-SHAPED PLANT VIRUS NANOPARTICLES AS IMAGING AGENT PLATFORMS

CROSS-REFERENCE TO RELATED APPLICATIONS

This application claims priority to U.S. Provisional Patent Application Ser. No. 61/711,492, filed Oct. 9, 2012, which is incorporated herein by reference.

GOVERNMENT FUNDING

The present invention was supported by NIH/NIBIB grant P30 EB011317 (to NFS)), Mt. Sinai Foundation (to NSF), and NIH/NHLBI training grant T32 HL105338. The Government has certain rights in this invention.

BACKGROUND

Magnetic resonance imaging (MRI) is an emerging technology used for detection of disease and for follow-up diagnosis after surgery or treatment. While MRI shows great potential because of its high spatial resolution, deep soft tissue contrast, and use of non-ionizing radiation, its low sensitivity remains a drawback. To overcome this shortcoming, paramagnetic contrast agents, such as Magnevist® (an FDA approved chelated gadolinium reagent), can be used to enhance the detection sensitivity of MRI. The conjugation of contrast agents to a macromolecular platform further enhances imaging sensitivity. Reduced molecular tumbling rates of gadolinium ions after conjugation to such nanoparticles results in increased longitudinal relaxivities. Waters, E. A. & Wickline, S. A., Basic Research in Cardiology, 103, 114-121 (2008). Furthermore, multivalent display results in increased local concentration, both events are contributing to increased sensitivity. Various nanoparticle systems have been explored as supramolecular contrast agents; these include dendrimers, liposomes, perfluorocarbons, silica, as well as protein cages and virus-based nanoparticles, also termed viral nanoparticles (VNPs). Bruckman, M, Steinmetz, N, "Engineering Gd-loaded nanoparticles to enhance MRI sensitivity via $T_1$ shortening," Nanotechnology, 24, (46) (2013).

VNPs, specifically plant viruses and bacteriophages, have received tremendous attention in recent years. They have been developed as research tools and platforms for materials science as well as for potential nanomedical applications. Lee et al., Biotechnol Bioeng. 109, 16-30 (2012). The propensity to self-assemble around a cargo (the genome) and to deliver this cargo to specific cells and tissues, make viruses ideal candidates for site-specific delivery of therapeutics and/or contrast agents. Indeed, several VNP-based technologies are in clinical testing for gene delivery and oncolytic virotherapy. VNPs are attractive materials because of their high degree of symmetry, polyvalency, monodispersity, and their genetic or chemical programmability. Most VNP structures have been solved to atomic resolution, which allows tailoring with a high degree of spatial control. Using chemoselective bioconjugation reactions, VNPs can be modified with imaging contrast agents, therapeutic moieties, and/or targeting ligands such as peptides or antibodies. For example, preclinical imaging of prostate tumors has been demonstrated using cowpea mosaic virus (CPMV) modified with prostate cancer-specific peptide ligands (bombesin) and near infrared imaging dyes. Steinmetz et al., Small 7, 1664-1672 (2011). Moving toward translational research, several research groups have engineering VNPs with paramagnetic MRI contrast agents. Similar to other nanoparticles, increased relaxivities are achieved based on reduced tumbling rate of the contrast agent. Huang et al., Theranostics 2, 86-102 (2012). For example, bacteriophage MS2, a 27 nm sphere, was loaded with ~180 chelated Gd molecules using a TOPO ligand and was able to achieve ionic relaxivities of up to 41.2 $mM^{-1}s^{-1}$ per Gd ion and 7,416 $mM^{-1}s^{-1}$ per nanoparticle. In comparison, Magnevist® has a relaxivity 5.2 $mM^{-1}s^{-1}$. Anderson et al. Nano Letters 6, 1160-1164 (2006); Garimella et al., JACS 133, 14704-14709 (2011).

To date, research and development of VNP-based MRI contrast agents has focused on spherical platforms; however, this may not be optimal. Recent work by the inventors and others indicates improved pharmacokinetics, increased immune evasion (e.g., reduced macrophage uptake), increased tumor homing, tissue penetration, and vessel wall targeting of elongated particles, e.g. potato virus X and tobacco mosaic virus Shukla et al. Molecular pharmaceutics, 10(1):33-42 (2013), Lee et al. Biomaterials Science 1, 581-588 (2013). Wen et al. Biological Physics, 39(2):301-25(2013). However, the use of rod-shaped virus particles as imaging agents remains unexplored.

SUMMARY

The inventors have explored the use of tobacco mosaic virus (TMV) as a scaffold for multivalent display of paramagnetic MRI contrast agents. TMV is a rod-shaped VNP measuring 300×18 nm with a solvent-accessible 4 nm-wide interior channel. What makes TMV particularly interesting is the recent discovery that TMV can undergo thermal transition to form RNA-free spherical nanoparticles (SNPs). Atabekov et al., Journal of General Virology 92, 453-456 (2011). The size of SNPs can be tightly tuned through adjustment of TMV concentration with sizes ranging from 100-300 nm (0.1-1.0 mg/ml) to 300-800 nm (1-10 mg/ml). TMV therefore provides a unique platform to study rod-shaped and spherical nanomaterials side-by-side.

Each TMV nanorod is formed from 2130 copies of an identical coat protein that is helically arranged around a single strand RNA. Klug, A., Philos Trans R Soc Lond B Biol Sci 354, 531-535 (1999). The rigid structure of TMV displays 2.2 times more coat proteins per cubic nanometer than its spherical (~30 nm diameter) VNP counterparts, thus allowing more efficient loading of cargos (contrast agents, therapeutics, and or targeting ligands). Engineering TMV particles has yielded a variety of materials for tissue engineering scaffolds, vaccine development, and a wide array of electronic materials. However, they have not previously been used as a drug delivery vehicle or contrast agent.

The inventors describe herein the formulation of a novel class of MRI contrast agents based on TMV nanorods and spheres. They show that contrast agent-loaded rod-shaped TMV can undergo thermal transition to form a spherical contrast agent. Conjugation of rod-shaped TMV with DOTA-Gd at either the exterior surface or interior channel was achieved using a combination of amide coupling, diazonium chemistry, and Cu(I)-catalyzed azide alkyne cycloaddition reactions. Particle modification and stability is confirmed with MALDI-TOF mass spectroscopy (MS), inductively coupled plasma optical emission spectrometry (ICP-OES), denaturing gel electrophoresis (SDS-PAGE), size exclusion chromatography (SEC), and transmission and scanning electron microscopy (TEM and SEM). Thermal re-shaping was then applied to generate high-relaxivity nanospheres. TMV rods with relaxivities up to ~35,000 mM$^{-1}$s$^{-1}$ and TMV SNPs with relaxivities of close to 400,000 mM$^{-1}$s$^{-1}$ were generated (measured at 60 MHz); these formulations display the highest relaxivities reported to date using VNP scaffolds. Finally, MR phantoms of varying concentrations were imaged using a pre-clinical 7.0T and a clinical 1.5T MRI.

In addition, a rod-shaped tobacco mosaic virus was used to target and image atherosclerotic plaques in vivo. TMV was loaded with magnetic resonance and fluorescence contrast agents to provide a dual-modal imaging platform. Targeting to atherosclerotic plaques was achieved with vascular cell adhesion molecule (VCAM) receptors present on activated endothelial cells. Dual, molecular imaging was confirmed using a mouse model of atherosclerosis.

BRIEF DESCRIPTION OF THE FIGURES

The present invention may be more readily understood by reference to the following drawings.

DETAILED DESCRIPTION

Figure 1:
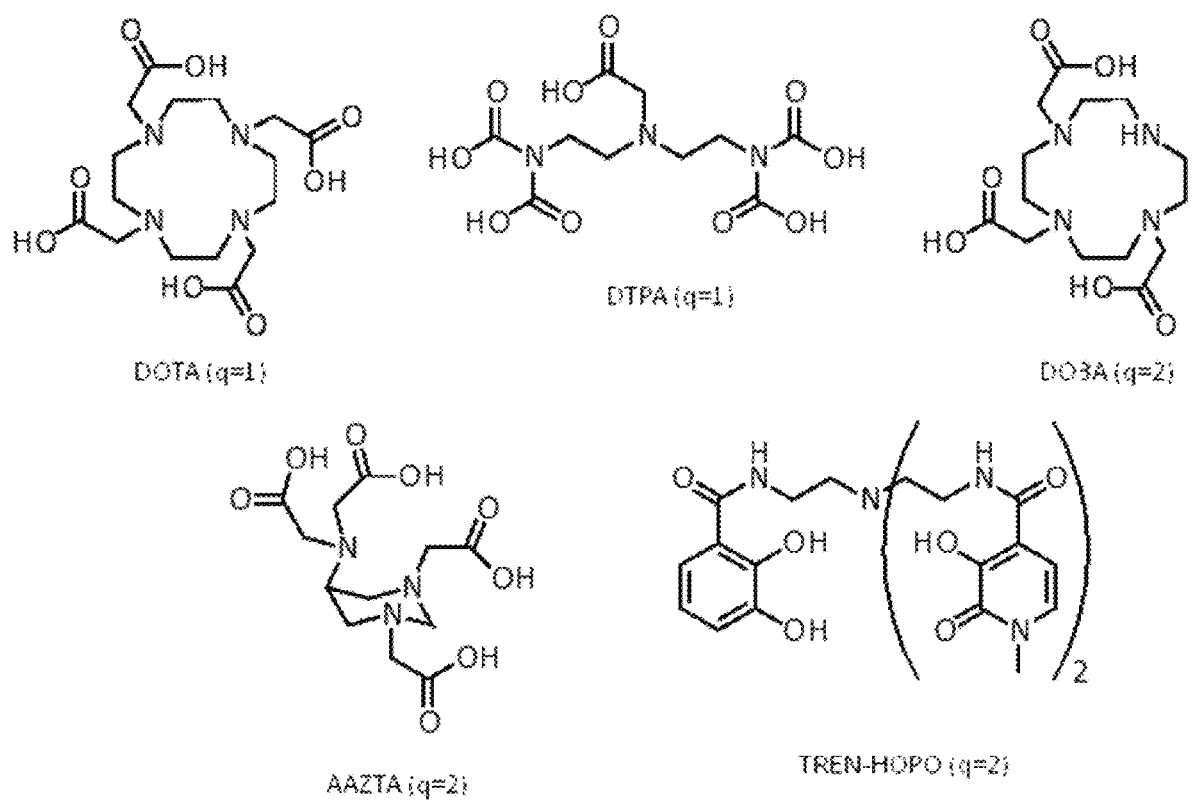
FIG. 1 provides the chemical structures of several common gadolinium (Gd) chelating molecules.

Rod-shaped plant viruses including at least one imaging agent that is linked to the interior and/or exterior surface of the virus are described. The rod-shaped viruses can be combined into spherical nanoparticles. The rod-shaped plant virus particles or spherical nanoparticles including an imaging agent can be used in a method of generating an image of a tissue region of a subject such as a tumor or atherosclerotic tissue by administering the virus particle to the subject and generating an image of the tissue region of the subject to which the virus particle has been distributed.

Definitions

It is to be understood that this invention is not limited to particular methods, reagents, compounds, compositions or biological systems, which can, of course, vary. It is also to be understood that the terminology used herein is for the purpose of describing particular embodiments only, and is not intended to be limiting. As used in this specification and the appended claims, the singular forms "a", "an" and "the" include plural references unless the content clearly dictates otherwise. Thus, for example, reference to "a cell" includes a combination of two or more cells, and the like.

The term "about" as used herein when referring to a measurable value such as an amount, a temporal duration, and the like, is meant to encompass variations of ±20% or 110%, more preferably ±5%, even more preferably ±1%, and still more preferably ±0.1% from the specified value, as such variations are appropriate to perform the disclosed methods.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

"Image" or "imaging" refers to a procedure that produces a picture of an area of the body, for example, organs, bones, tissues, or blood.

A "subject," as used herein, can be any animal, and may also be referred to as the patient. Preferably the subject is a vertebrate animal, and more preferably the subject is a mammal, such as a domesticated farm animal (e.g., cow, horse, pig) or pet (e.g., dog, cat). In some embodiments, the subject is a human.

"Pharmaceutically acceptable" as used herein means that the compound or composition is suitable for administration to a subject for the methods described herein, without unduly deleterious side effects.

As used herein, the term "relaxation time" refers to the time required for a nucleus which has undergone a transition into a higher energy state to return to the energy state from which it was initially excited. Regarding bulk phenomena, the term "relaxation time" refers to the time required for a sample of nuclei, the Boltzmann distribution of which has been perturbed by the application of energy, to reestablish the Boltzmann distribution. The relaxation times are commonly denoted $T_1$ and $T_2$. $T_1$ is referred to as the longitudinal relaxation time and $T_2$ is referred to as the transverse relaxation time. As used herein, the term "relaxation time" refers to the above-described relaxation times either together or in the alternative. An exhaustive treatise on nuclear relaxation is available in Banci, L, et al. Nuclear and Electron Relaxation, VCH, Weinheim, 1991, which is herein incorporated by reference.

As used herein, the term "diagnostically effective amount" refers to an amount of contrast agent that is sufficient to enable imaging of the contrast agent in cells, tissues, or organisms using imaging equipment.

In one aspect, the present invention provides a rod-shaped plant virus having an interior surface and an exterior surface, and at least one imaging agent that is linked to the interior and/or exterior surface of the virus.

Rod-Shaped Plant Viruses

A rod-shaped plant virus is a virus that primarily infects plants, is non-enveloped, and is shaped as a rigid helical rod with a helical symmetry. Rod shaped viruses also include a central canal. Rod-shaped plant virus particles are distinguished from filamentous plant virus particles as a result of being inflexible, shorter, and thicker in diameter. For example, Virgaviridae have a length of about 200 to about 400 nm, and a diameter of about 15-25 nm. Virgaviridae have other characteristics, such as having a single-stranded RNA positive sense genome with a 3'-tRNA like structure and no polyA tail, and coat proteins of 19-24 kilodaltons.

In some embodiments, the rod-shaped plant virus belongs to a specific virus family, genus, or species. For example, in some embodiments, the rod-shaped plant virus belongs to the Virgaviridae family. The Virgaviridae family includes the genus Furovirus, Hordevirus, Pecluvirus, Pomovirus, Tobamovirus, and Tobravirus. In some embodiments, the rod-shaped plant virus belongs to the genus Tobamovirus. In further embodiments, the rod-shaped plant virus belongs to the tobacco mosaic virus species. The tobacco mosaic virus has a capsid made from 2130 molecules of coat protein and one molecule of genomic single strand RNA 6400 bases long. The coat protein self-assembles into the rod like helical structure (16.3 proteins per helix turn) around the RNA which forms a hairpin loop structure. The protein monomer consists of 158 amino acids which are assembled into four main alpha-helices, which are joined by a prominent loop proximal to the axis of the virion. Virions are ~300 nm in length and ~18 nm in diameter. Negatively stained electron microphotographs show a distinct inner channel of ~4 nm.

Figure 4:
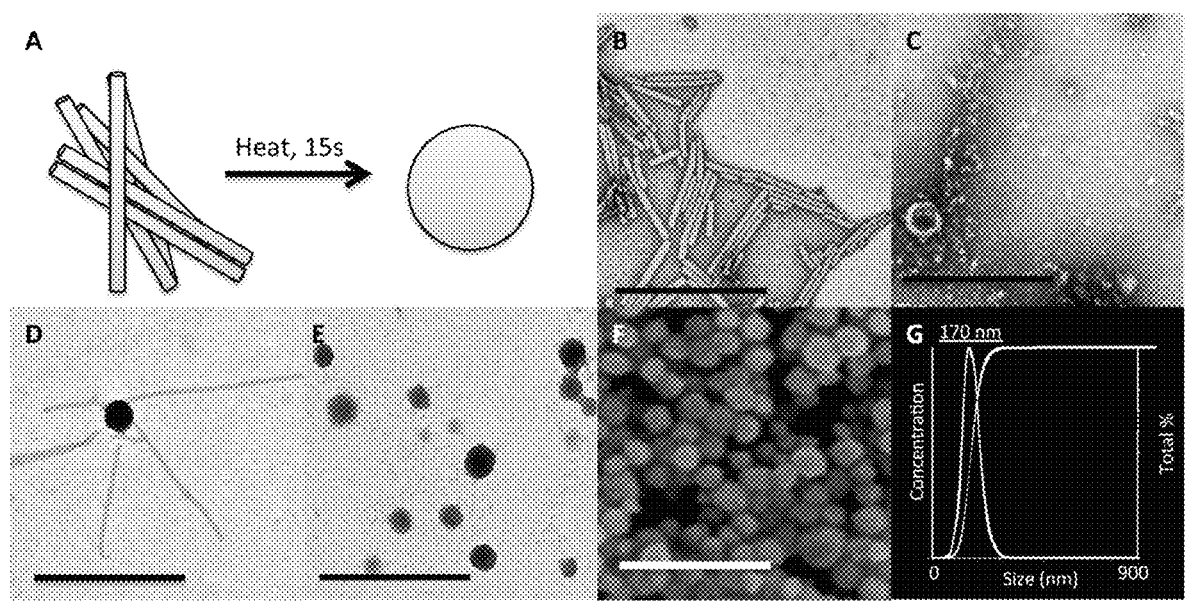
FIG. 4 provides (A) schematic illustration of the thermal transition from rod-shaped TMV to spherical nanoparticles; representative TEM images of (B) iGd-TMV, (C) eGd-TMV to SNP, (D) iGd-TMV to SNP, 10 seconds, and (E) iGd-TMV to SNP 15 seconds; and (F) SEM image of iGd-SNPs with (G) the corresponding DLS (Nanosight size analyzer). Scale bars=500 nm.

In further embodiments, the rod-shaped plant virus particle can be combined with other rod-shaped plant virus particles by means of a thermal transition to form an RNA-free spherical nanoparticle (SNP), also referred to herein as a spherical nanoparticle imaging platform. FIG. 4 provides a schematic illustration of the thermal transition from rod-shaped virus particles to spherical nanoparticles. A spherical nanoparticle imaging platform is a spherical arrangement of the coat proteins of a plurality of rod-shaped plant virus particles linked to an imaging agent on an interior surface of the virus particle, formed by thermal transition of the rod-shaped virus particles. The SNPs can be formed from rod-shaped plant virus particles bearing imaging agents linked to the interior surface of the rod-shaped plant virus particles. SNPs can be labeled with suitable chemicals prior or post thermal transition; for example, NHS-based chemistries allow one to conjugate functional molecules to SNPs post thermal transition; the SNPs are stable and remain structurally sound after chemical modification. The SNPs including imaging agent can be formed from rod-shaped plant virus particles (e.g., TMV virus particles) by briefly heating the rod-shaped plant virus particles labeled with imaging agent on an interior surface of the virus particle. For example, the rod-shaped plant virus particles can be induced to undergo a thermal transition into SNPs by heating at about 96° C. for about 10 to about 20 seconds. Examples of suitable rod-shaped virus particles include Virgaviridae virus particles and tobacco mosaic virus particles. Any of the imaging agents described herein can be used with the spherical nanoparticles. In some embodiments, the imaging agent is a chelated lanthanide such as gadolinium.

The SNPs are formed from the coat proteins of one or more individual rod-shaped plant virus particles. In various embodiments, the SNP can be formed from about 1 to 10 virus particles, from about 10 to about 20 virus particles, from about 20 to about 30 virus particles, from about 30 to about 40 virus particles, or from about 40 to about 50 virus particles. Depending on the nature of the coat proteins, the number of virus particles incorporated, and the virus particle concentration in the solution in which the thermal transition occurs, the spherical nanoparticles can also vary in size. In some embodiments, the SNPs have a size from about 50 nm to about 800 nm. In further embodiments, the SNPs have a size from about 100 to about 300 nm, or from about 150 to about 200 nm.

Spherical nanoparticles including imaging agents such as chelated gadolinium provide several advantages. First, SNPs can include a high per-particle concentration of imaging agent. For example, SNPs can include from about 3,000 to about 30,000 imaging agents per spherical nanoparticle, with about 20,000 to about 30,000 imaging agent molecules per spherical nanoparticle in some embodiments. In addition, for MRI imaging agents such as chelated lanthanides, the SNPs including imaging agents can also exhibit very high relaxivity per particle. For example, SNPs including lanthanide imaging agents can exhibit a $T_1$ relaxivity per particle from about 10,000 mM$^{-1}$s$^{-1}$ to about 500,000 mM$^{-1}$s$^{-1}$ at 60 MHz, with about 350,000 mM$^{-1}$s$^{-1}$ to about 450,000 mM$^{-1}$s$^{-1}$ at 60 MHz in some embodiments. Finally, SNPs are more rapidly cleared from the body, which can be advantageous with imaging agents that may have increased adverse side effects when they persist within the subject after imaging.

Imaging Agents

The rod-shaped plant virus particle is modified to carry an imaging agent; i.e., the plant virus carrier comprises an imaging agent. Examples of imaging agents include fluorescent compounds, radioactive isotopes, and MRI contrast agents. For example, in some embodiments, the imaging agent is a fluorescent molecule for fluorescent imaging. The detectable group can be any material having a detectable physical or chemical property. Such imaging agents have been well-developed in the field of fluorescent imaging, magnetic resonance imaging, positive emission tomography, or immunoassays and, in general, most any imaging agent useful in such methods can be applied to the present invention. Thus, an imaging agent is any composition detectable by spectroscopic, photochemical, biochemical, immunochemical, electrical, optical or chemical means. Useful imaging agents in the present invention include magnetic beads (e.g. Dynabeads™), fluorescent dyes (e.g., fluorescein isothiocyanate, AlexaFluor555, Texas red, rhodamine, and the like), radiolabels (e.g., $^{3}H$, $^{14}C$, $^{35}S$, $^{125}I$, $^{121}I$, $^{112}In$, $^{99m}Tc$), other imaging agents such as microbubbles (for ultrasound imaging), $^{18}F$, $^{11}C$, $^{15}O$, (for Positron emission tomography), $^{99m}TC$, $^{111}In$ (for single photon emission tomography), and chelated lanthanides such as terbium, gadoliniuum, and europium (e.g., chelated gadolinium) or iron (for magnetic resonance imaging). The choice of imaging agent depending on sensitivity required, ease of conjugation with the compound, stability requirements, available instrumentation, and disposal provisions.

In some embodiments, the imaging agent is a magnetic resonance imaging agent. Disease detection using MRI is often difficult because areas of disease have similar signal intensity compared to surrounding healthy tissue. In the case of magnetic resonance imaging, the imaging agent can also be referred to as a contrast agent. Lanthanide elements are known to be useful as contrast agents. The lanthanide chemical elements comprises the fifteen metallic chemical elements with atomic numbers 57 through 71, and include lanthanum, cerium, praseodymium, neodymium, promethium, samarium, europium, gadolinium, terbium, dysprosium, holmium, erbium, thulium, ytterbium, and lutetium. Preferred lanthanides include europium, gadolinium, and terbium. In order to more readily handle these rare earth metals, the lanthanides are preferably chelated. In some embodiments, the lanthanide selected for use as a contrast agent is gadolinium, or more specifically gadolinium (III).

Contrast agents are used to enhance the differentiation between tissue regions in order to better image the tissue. The ionic relaxivity rate of a contrast agent describes its capacity for contrast enhancement. The relaxivity rate can be affected by a number of factors, including the use of a chelating agent. Unless indicated otherwise, all relaxivity measurements described herein are at 60 MHz, which is the field strength at which the relaxivity was typically measured. A clinical 3.0 Tesla magnet measures at that field strength. However, it should be noted that preclinical imaging is often done at higher magnetic field strength, and that the relaxivity can change with the field strength. The relaxivity rate per rod-shaped plant virus particle can also be increased by increasing the number of agent molecules that are linked to the virus particle. Rod-shaped plant virus particles of the invention that have been chemically modified to include contrast agents can exhibit relaxivity rates from about 10,000 to about 40,000 $mM^{-1}S^{-1}$. In some embodiments, the virus particles bearing contrast agents exhibit $T_1$ relaxivity rates of at least about 10,000 $mM^{-1}S^{-1}$, about 20,000 $mM^{-1}S^{-1}$, about 25,000 $mM^{-1}S^{-1}$, about 30,000 $mM^{-1}S^{-1}$, about 35,000 $mM^{-1}S^{-1}$, and about 40,000 $mM^{-1}S^{-1}$ at 60 MHz.

Non-radioactive labels are often attached by indirect means. Generally, a ligand molecule (e.g., biotin) is covalently bound to the virus particle. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands can be used. Where a ligand has a natural anti-ligand, for example, biotin, thyroxine, and cortisol, it can be used in conjunction with the labeled, naturally occurring anti-ligands.

Conjugation of Imaging Agents

The invention makes use of a rod-shaped plant virus particle that has been modified to carry an imaging agent. Including an imaging agent allows the virus particle to serve as a platform for the imaging agent. A rod-shaped plant virus (i.e., rod-shaped plant virus particle) that has been modified to include an imaging agent is also referred to herein as a rod-shaped plant virus carrier.

In general, imaging agents can be conjugated to the rod-shaped plant virus by any suitable technique, with appropriate consideration of the need for pharmacokinetic stability and reduced overall toxicity to the patient. The term "conjugating" when made in reference to an agent and a rod-shaped plant virus particle as used herein means covalently linking the agent to the virus subject to the single limitation that the nature and size of the agent and the site at which it is covalently linked to the virus particle do not interfere with the biodistribution of the modified virus. The imaging agent can be linked to the interior or the exterior of the virus, while in some embodiments the imaging agent is linked to both the interior and the exterior of the virus. The location of the imaging agent on the interior or exterior is governed by the amino acids of the viral coat protein that are selected as target linking sites.

An imaging agent can be coupled to a rod-shaped plant virus particle either directly or indirectly (e.g. via a linker group). In some embodiments, the agent is directly attached to a functional group capable of reacting with the agent. For example, viral coat proteins include lysines that have a free amino group that can be capable of reacting with a carbonyl-containing group, such as an anhydride or an acid halide, or with an alkyl group containing a good leaving group (e.g., a halide). Viral coat proteins also contain glutamic and aspartic acids. The carboxylate groups of these amino acids also present attractive targets for functionalization using carbodiimide activated linker molecules; cysteines can also be present which facilitate chemical coupling via thiol-selective chemistry (e.g., maleimide-activated compounds). Further, viral coat proteins contain tyrosines, which can be modified using diazonium coupling reactions. In addition, genetic modification can be applied to introduce any desired functional residue, including non-natural amino acids, e.g. alkyne- or azide-functional groups. See Hermanson, G. T. Bioconjugation Techniques. (Academic Press, 2008) and Pokorski, J. K. and N. F. Steinmetz, Mol Pharm 8(1): 29-43 (2011), the disclosures of which are incorporated herein by reference.

Alternatively, a suitable chemical linker group can be used. A linker group can serve to increase the chemical reactivity of a substituent on either the agent or the virus particle, and thus increase the coupling efficiency. Suitable linkage chemistries include maleimidyl linkers, which can be used to link to thiol groups, isothiocyanate and succinimidyl (e.g., N-hydroxysuccinimidyl (NHS)) linkers, which can link to free amine groups, diazonium which can be used to link to phenol, and amines, which can be used to link with free acids such as carboxylate groups using carbodiimide activation. Useful functional groups are present on viral coat proteins based on the particular amino acids present, and additional groups can be designed into recombinant viral coat proteins. It will be evident to those skilled in the art that a variety of bifunctional or polyfunctional reagents, both homo- and hetero-functional (such as those described in the catalog of the Pierce Chemical Co., Rockford, Ill.), can be employed as a linker group. Coupling can be effected, for example, through amino groups, carboxyl groups, sulfhydryl groups or oxidized carbohydrate residues.

Other types of linking chemistries are also available. For example, methods for conjugating polysaccharides to peptides are exemplified by, but not limited to coupling via alpha- or epsilon-amino groups to $NaIO_4$-activated oligosaccharide (Bocher et al., J. Immunol. Methods 27, 191-202 (1997)), using squaric acid diester (1,2-diethoxycyclobutene-3,4-dione) as a coupling reagent (Tietze et al. Bioconjug Chem. 2:148-153 (1991)), coupling via a peptide linker wherein the polysaccharide has a reducing terminal and is free of carboxyl groups (U.S. Pat. No. 5,342,770), and coupling with a synthetic peptide carrier derived from human heat shock protein hsp65 (U.S. Pat. No. 5,736,146). Further methods for conjugating polysaccharides, proteins, and lipids to plant virus peptides are described by U.S. Pat. No. 7,666,624.

When attaching lanthanide imaging agents such as gadolinium ions a chelating compound is also used. Conjugation of a chelated lanthanide ion to a virus particle can decrease its molecular tumbling rate, resulting in an increased ionic relaxivity rate. A number of chelating compounds have been developed to increase the coordinated water molecules for lanthanide ions, which can almost double the relaxivity rate. Examples of effective gadolinium chelating molecules include 1,4,7,10-tetraazacyclododecane-1,4,7,10-tetraacetic acid (DOTA), diethylenetriaminopentacetate (DTPA), 1,4,7,10-tetraazacyclododecane-1,4,7-triasacetic acid (DO3A), 6-amino-6-methylperhydro-1,4-diazepinetetraacetic acid (AAZTA), and 4-carboxyamido-3,2-hydroxypyridinone (HOPA), which are shown in FIG. 1. See Gugliotta et al., Org. Biomol. Chem., 8, 4569 (2010), the disclosure of which is incorporated herein by reference. Bifunctional chelating agents including N-hydroxysuccinimide/isothiocyanates, amine, maleimide, and azide chemical linkers can be used for conjugation to amines, carboxylic acids, thiols, and alkynes.

Figure 3:
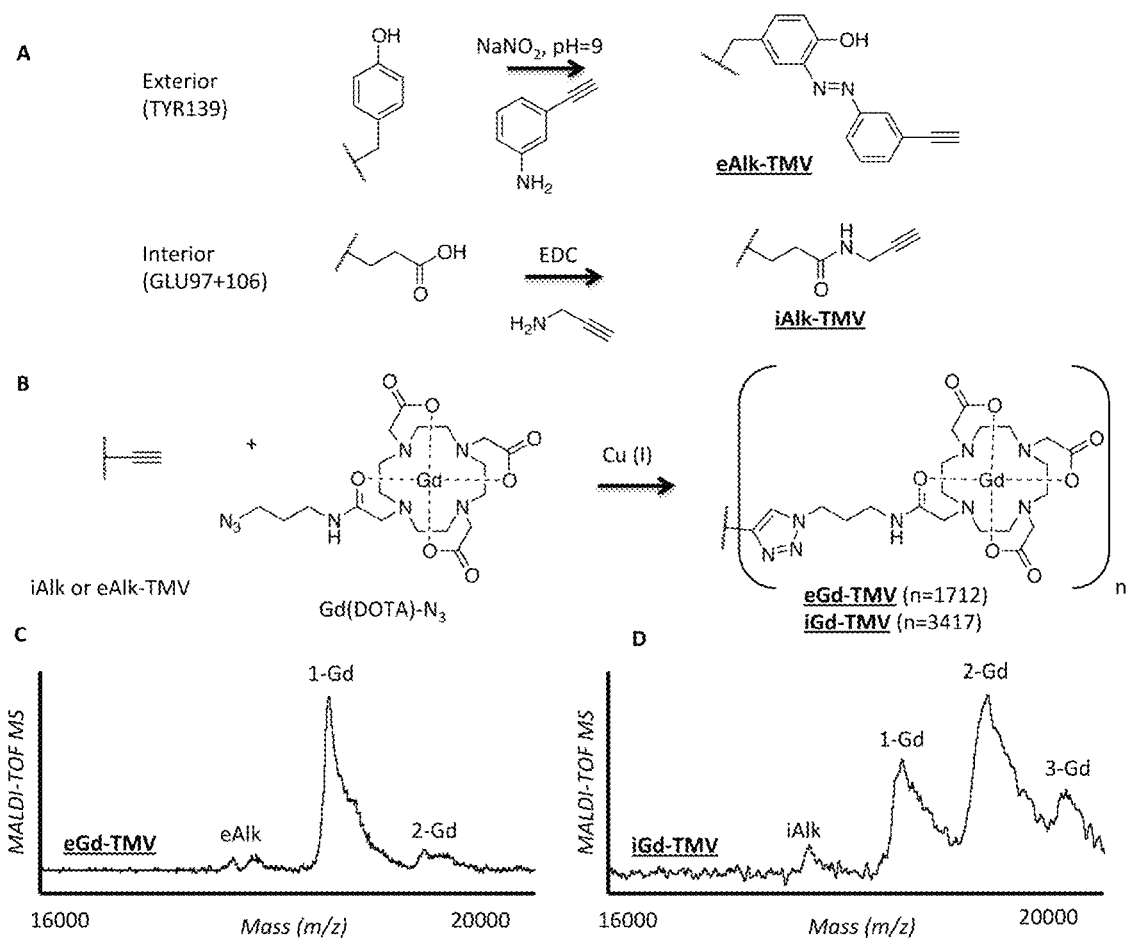
FIG. 3 provides (A) schematic illustration of the bioconjugation reactions used to incorporate terminal alkynes to the interior and exterior of TMV; (B) schematic illustration of the CuAAC reaction to label TMV particles with Gd(DOTA); and MALDI-TOF MS of (C) eGd-TMV and (D) iGd-TMV. In the MALDI-TOF MS, peaks labeled with eAlk and iAlk refer to the alkyne labeled proteins, 1-Gd, 2-Gd, and 3-Gd refer to coat proteins labeled with one, two, and three Gd(DOTA).

In some embodiments, more than one type of imaging agent can be attached to a rod-shaped plant virus particle. For example, a rod-shaped virus particle can be made useful as an imaging agent for two or more different visualization techniques. In further embodiments, differences in the linking sites available on the outside surface (i.e., exterior) and inside channel (i.e., interior) of the virus particle can be used to provide a virus particle with different imaging agents on the inside and outside of the virus particle. For example, the virus particle can have a first imaging agent on the inside of the particle, and a second, different imaging agent on the outside of the virus particle. The different linking sites allow different linking chemistries to be used for the interior and exterior portions of the virus particle. For example, as shown in FIG. 3, diazonium chemistry can be used to attach agents to phenol groups that are accessible on the exterior of a virus particle, while amine chemistry is used to attach agents to carboxyl groups present on the interior of the virus particle. In further embodiments, rather than including a different imaging agent, different linking sites can be used to attach a therapeutic agent and/or a targeting moiety to the virus particle.

One advantage of the rod-shaped virus particles of the present invention is that they have a higher number of coat proteins per cubic nanometer as compared with other viral particles, allowing more efficient loading of imaging agents onto the virus particle. The number of imaging agents that can be loaded onto the virus particle depends on the number of attachment sites available and the chemistries employed to link the agents to the virus particle. In some embodiments, each virus particle is loaded with about 500 agent molecules. In further embodiments, each virus particle is loaded with at least about 1,000, 1,500, 2,000, 2,500, 3,000, 3,500, 4,000, 4,500, or at least about 5,000 imaging agent molecules.

Targeting Moieties

In some embodiments, a targeting moiety can also be attached to the rod-shaped plant virus particle. By "targeting moiety" herein is meant a functional group which serves to target or direct the virus particle to a particular location, cell type, diseased tissue, or association. In general, the targeting moiety is directed against a target molecule. Thus, for example, antibodies, cell surface receptor ligands and hormones, lipids, sugars and dextrans, alcohols, bile acids, fatty acids, amino acids, peptides and nucleic acids may all be attached to localize or target the virus particle to a particular site. In some embodiments, the targeting moiety allows targeting of the rod-shaped plant virus particles of the invention to a particular tissue or the surface of a cell. Preferably, the targeting moiety is linked to the exterior surface of the virus to provide easier access to the target molecule.

In some embodiments, the targeting moiety is a peptide. For example, chemotactic peptides have been used to image tissue injury and inflammation, particularly by bacterial infection; see WO 97/14443, hereby expressly incorporated by reference in its entirety. Another example, are peptides specific to fibrin or vascular cell adhesion molecules to direct the imaging probe to sites of inflammation, such as an atherosclerotic plaque. In other embodiments, the targeting moiety is an antibody. The term "antibody" includes antibody fragments, as are known in the art, including Fab $Fab_2$, single chain antibodies (Fv for example), chimeric antibodies, etc., either produced by the modification of whole antibodies or those synthesized de novo using recombinant DNA technologies. In further embodiments, the antibody targeting moieties of the invention are humanized antibodies or human antibodies. Humanized forms of non-human (e.g., murine) antibodies are chimeric immunoglobulins, immunoglobulin chains or fragments thereof (such as Fv, Fab, Fab', $F(ab')_2$ or other antigen-binding subsequences of antibodies) which contain minimal sequence derived from non-human immunoglobulin.

In some embodiments, the antibody is directed against a cell-surface marker on a cancer cell; that is, the target molecule is a cell surface molecule. As is known in the art, there are a wide variety of antibodies known to be differentially expressed on tumor cells, including, but not limited to, HER2. Examples of physiologically relevant carbohydrates may be used as cell-surface markers include, but are not limited to, antibodies against markers for breast cancer (CA 15-3, CA 549, CA 27.29), mucin-like carcinoma associated antigen (MCA), ovarian cancer (CA125), pancreatic cancer (DE-PAN-2), and colorectal and pancreatic cancer (CA 19, CA 50, CA242).

In some embodiments, the targeting moiety is all or a portion (e.g. a binding portion) of a ligand for a cell surface receptor. Suitable ligands include, but are not limited to, all or a functional portion of the ligands that bind to a cell surface receptor selected from the group consisting of insulin receptor (insulin), insulin-like growth factor receptor (including both IGF-1 and IGF-2), growth hormone receptor, glucose transporters (particularly GLUT 4 receptor), transferrin receptor (transferrin), epidermal growth factor receptor (EGF), low density lipoprotein receptor, high density lipoprotein receptor, leptin receptor, estrogen receptor (estrogen); interleukin receptors including IL-1, IL-2, IL-3, IL-4, IL-5, IL-6, IL-7, IL-8, IL-9, IL-11, IL-12, IL-13, IL-15, and IL-17 receptors, human growth hormone receptor, VEGF receptor (VEGF), PDGF receptor (PDGF), transforming growth factor receptor (including TGF-α and TGF-β), EPO receptor (EPO), TPO receptor (TPO), ciliary neurotrophic factor receptor, prolactin receptor, and T-cell receptors. Receptor ligands include ligands that bind to receptors such as cell surface receptors, which include hormones, lipids, proteins, glycoproteins, signal transducers, growth factors, cytokines, and others.

In some embodiments, the rod-shaped plant virus is used to target tissue in a subject without the use of a targeting moiety based on the ability of rod-shaped plant virus particles to preferentially accumulate in certain tissues. In particular, the rod-shaped plant virus particles have been shown to preferentially accumulate in diseased tissue, such as cancer tissue or inflamed tissue (e.g., atherosclerotic blood vessels). While not intending to be bound by theory, it appears that rod-shaped plant virus particles are taken up by blood components such as macrophage cells of the immune system, which subsequently accumulate in diseased tissue (e.g., a tumor or atherosclerotic blood vessel), thereby delivering the rod-shaped plant virus to cells at the disease site.

A tumor is an abnormal mass of tissue as a result of abnormal growth or division of cells caused by cancer. Tumors can occur in a variety of different types of tissue such as the breast, lung, brain, liver kidney, colon, and prostate, can be malignant or benign, and generally vary in size from about 1 cm to about 5 cm.

Magnetic resonance angiography (MRA) is a type of MRI that generates pictures of blood vessels (e.g., arteries) to evaluate them for stenosis (abnormal narrowing) or aneurysms (vessel wall dilatations, at risk of rupture). MRA can be used to evaluate the arteries of the neck and brain, the thoracic and abdominal aorta, the renal arteries, and the legs. Rod-shaped plant virus particles (or SNPs) including linked imaging agents can be used to facilitate conducing MRA of blood vessels for various uses, including evaluation of the possible development of atherosclerosis. Atherosclerosis is a chronic inflammatory response in the walls of arteries, caused largely by the accumulation of macrophages and white blood cells and promoted by low-density lipoproteins (LDL, plasma proteins that carry cholesterol and triglycerides) without adequate removal of fats and cholesterol from the macrophages by functional high-density lipoproteins (HDL). It is commonly referred to as a hardening or furring of the arteries, and is caused by the formation of multiple plaques within the arteries, which can be detected by MRA.

Imaging a Tissue Region

In one aspect, the present invention provides a method of generating an image of a tissue region of a subject, by administering to the subject a diagnostically effective amount of a rod-shaped plant virus particle having an imaging agent linked to an interior and/or exterior surface of the virus particle, and generating an image of the tissue region of the subject to which the rod-shaped plant virus particle has distributed. In order to generate an image of the tissue region, it is necessary for an effective amount of imaging agent to reach the tissue region of interest, but it is not necessary that the imaging agent be localized in this region alone. However, in some embodiments, the virus particles bearing imaging agents are targeted or administered locally such that they are present primarily in the tissue region of interest. In some embodiments, SNPs formed from rod-shaped plant virus particles are used instead of rod-shaped plant virus particles. Examples of images include two-dimensional cross-sectional views and three dimensional images. In some embodiments, a computer is used to analyze the data generated by the imaging agents in order to generate a visual image. The rod-shaped plant virus particles can include any of the virus particles described herein, such as Virgaviridae virus particles and tobacco mosaic virus particles. The tissue region can be an organ of a subject such as the heart, lungs, or blood vessels. In other embodiments, the tissue region can be diseased tissue, or tissue that is suspected of being diseased, such as a tumor or atherosclerotic tissue. Examples of imaging methods include fluoroscopy, computed tomography, positive emission tomography, and magnetic resonance imaging.

Means of detecting labels in order to generate an image are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Finally simple colorimetric labels may be detected simply by observing the color associated with the label.

"Computed tomography (CT)" refers to a diagnostic imaging tool that computes multiple x-ray cross sections to produce a cross-sectional view of the vascular system, organs, bones, and tissues. "Positive emissions tomography (PET)" refers to a diagnostic imaging tool in which the patient receives a radioactive isotopes by injection or ingestion which then computes multiple x-ray cross sections to produce a cross-sectional view of the vascular system, organs, bones, and tissues to image the radioactive tracer. These radioactive isotopes are bound to compounds or drugs that are injected into the body and enable study of the physiology of normal and abnormal tissues. "Magnetic resonance imaging (MRI)" refers to a diagnostic imaging tool using magnetic fields and radiowaves to produce a cross-sectional view of the body including the vascular system, organs, bones, and tissues. Suitable imaging agents should be used that will help generate an image of a tissue region in the context of the imaging technique being used. For example, when using magnetic resonance imaging, a suitable imaging agent is a chelated lanthanide.

In some embodiments, the viral imaging agents (rod-shaped and SNP) of the present invention are used for MRI. MRI provides a good contrast between the different soft tissues of the body, which makes it especially useful in imaging the brain, muscles, the heart, and cancers compared with other medical imaging techniques such as computed tomography or X-rays. An MRI scanner is a device in which the subject lies within a large, powerful magnet where the magnetic field is used to align the magnetization of some atomic nuclei in the body, and radio frequency magnetic fields are applied to systematically alter the alignment of this magnetization. This causes the nuclei to produce a rotating magnetic field detectable by the scanner and this information is recorded to construct an image of a tissue region. Magnetic field gradients cause nuclei at different locations to precess at different speeds, which allows spatial information to be recovered using Fourier analysis of the measured signal. By using gradients in different directions, 2D images or 3D volumes can be obtained in any arbitrary orientation Various different types of MRI scans can be conducted, including $T_1$-weighted MRI, $T_2$-weighted MRI, and spin density weighted MRI. In some embodiments, the viral imaging agents of the invention are used as contrast agents to facilitate a T1-weighted MRI scan. $T_1$-weighted scans refer to a set of standard scans that depict differences in the spin-lattice (or T1) relaxation time of various tissues within the body. $T_1$ weighted images can be acquired using either spin echo or gradient-echo sequences. $T_1$-weighted contrast can be increased with the application of an inversion recovery RF pulse. Gradient-echo based $T_1$-weighted sequences can be acquired very rapidly because of their ability to use short inter-pulse repetition times (TR).

Pharmacokinetics and Immune Response to Virus Particles

In some embodiments, administering the rod-shaped plant virus carrier to a subject can generate an immune response. An "immune response" refers to the concerted action of lymphocytes, antigen presenting cells, phagocytic cells, granulocytes, and soluble macromolecules produced by the above cells or the liver (including antibodies, cytokines, and complement) that results in selective damage to, destruction of, or elimination from the human body of cancerous cells, metastatic tumor cells, invading pathogens, cells or tissues infected with pathogens, or, in cases of autoimmunity or pathological inflammation, normal human cells or tissues. Components of an immune response can be detected in vitro by various methods that are well known to those of ordinary skill in the art.

Generation of an immune response by the rod-shaped plant virus carrier is typically undesirable. Accordingly, in some embodiments it may be preferable to modify the rod-shaped plant virus carrier or take other steps to decrease the immune response. For example, an immunosuppressant compound can be administered to decrease the immune response. More preferably, the rod-shaped plant virus carrier can be modified to decrease its immunogenicity. Examples of methods suitable for decreasing immunity include attachment of anti-fouling (e.g., zwitterionic) polymers, glycosylation of the virus carrier, and PEGylation.

In some embodiments, the immunogenicity of the rod-shaped plant virus is decreased by PEGylation to provide a PEGylated rod-shaped plant virus. PEGylation is the process of covalent attachment of polyethylene glycol (PEG) polymer chains to a molecule such as a rod-shaped plant virus carrier. PEGylation can be achieved by incubation of a reactive derivative of PEG with the rod-shaped plant virus carrier. The covalent attachment of PEG to the rod-shaped plant virus carrier can "mask" the agent from the host's immune system, and reduce production of antibodies against the carrier. PEGylation also may provide other benefits. PEGylation can be used to vary the circulation time of the rod-shaped plant virus carrier. For example, use of PEG 5,000 can provide a virus carrier with a circulation half-life of about 12.5 minutes, while use of PEG 20,000 can provide a virus carrier with a circulation half life of about 110 minutes.

The first step of PEGylation is providing suitable functionalization of the PEG polymer at one or both terminal positions of the polymer. The chemically active or activated derivatives of the PEG polymer are prepared to attach the PEG to the rod-shaped plant virus carrier. There are generally two methods that can be used to carry out PEGylation; a solution phase batch process and an on-column fed-batch process. The simple and commonly adopted batch process involves the mixing of reagents together in a suitable buffer solution, preferably at a temperature between 4 and 6° C., followed by the separation and purification of the desired product using a chromatographic technique.

A significantly higher dose of rod-shaped plant virus particles remains in circulation over longer time periods compared to spherical nanoparticles (SNPs). At 60 minutes post i.v. administration of tobacco mosaic virus (TMV) vs. SNP, 20% injected dose (ID) TMV remained in circulation, while only 5% ID SNPs were detected. This is reflected by the increased phase II half-lives of 94.9 minutes for TMV and 58.2 minutes for SNPs. This phenomenon has been reported using various synthetic nanoparticle systems: for example synthetic polymeric filomicelles show enhanced circulation compared to spherical micelles made of the same polymer, and could be explained by the fact that the high aspect ratio materials are less likely taken up by MPS. Geng et al., Nature Nanotechnology 2, 249-255 (2007). There is increasing supporting data showing that elongated particles avoid clearance by phagocytosis because of their larger and more complex contact angles between the nanoparticle and phagocytotic cell. This has been demonstrated with gold nanoparticles where the circulation half-life of rods was significantly longer than their spherical shaped counterpart. Arnida et al., Eur. J. Pharm. Biopharm. 77, 417-423 (2011).

Administration and Formulation of Rod-Shaped Plant Virus Carriers

In some embodiments, the rod-shaped plant virus carrier is administered together with a pharmaceutically acceptable carrier to provide a pharmaceutical formulation. Pharmaceutically acceptable carriers enable the rod-shaped plant virus carrier to be delivered to the subject in an effective manner while minimizing side effects, and can include a variety of diluents or excipients known to those of ordinary skill in the art. Formulations include, but are not limited to, those suitable for oral, rectal, vaginal, topical, nasal, ophthalmic, or parental (including subcutaneous, intramuscular, intraperitoneal, intratumoral, and intravenous) administration. For example, for parenteral administration, isotonic saline is preferred. For topical administration, a cream, including a carrier such as dimethylsulfoxide (DMSO), or other agents typically found in topical creams that do not block or inhibit activity of the compound, can be used. Other suitable carriers include, but are not limited to, alcohol, phosphate buffered saline, and other balanced salt solutions.

The formulations may be conveniently presented in unit dosage form and may be prepared by any of the methods well known in the art of pharmacy. Preferably, such methods include the step of bringing the rod-shaped plant virus carrier into association with a pharmaceutically acceptable carrier that constitutes one or more accessory ingredients. In general, the formulations are prepared by uniformly and intimately bringing the active agent into association with a liquid carrier, a finely divided solid carrier, or both, and then, if necessary, shaping the product into the desired formulations. The methods of the invention include administering to a subject, preferably a mammal, and more preferably a human, the composition of the invention in an amount effective to produce the desired effect. The formulated virus carrier can be administered as a single dose or in multiple doses.

Useful dosages of the active agents can be determined by comparing their in vitro activity and the in vivo activity in animal models. Methods for extrapolation of effective dosages in mice, and other animals, to humans are known in the art; for example, see U.S. Pat. No. 4,938,949. An amount adequate to accomplish therapeutic or prophylactic treatment is defined as a therapeutically- or prophylactically-effective dose. In both prophylactic and therapeutic regimes, agents are usually administered in several dosages until an effect has been achieved. Effective doses of the rod-shaped plant virus carrier vary depending upon many different factors, including means of administration, target site, physiological state of the patient, whether the patient is human or an animal, other medications administered, and whether treatment is prophylactic or therapeutic.

For administration for targeting or imaging in a mammalian subject utilizing a rod-shaped plant virus carrier, the dosage of the imaging agent ranges from about 0.0001 to 100 mg/kg, and more usually 0.01 to 5 mg/kg, of the host body weight. For example dosages can be 1 mg/kg body weight or 10 mg/kg body weight or within the range of 1-10 mg/kg. A suitable amount of virus particle is used to provide the desired dosage. An exemplary treatment regime entails administration once per every two weeks or once a month or once every 3 to 6 months. The rod-shaped plant virus carrier is usually administered on multiple occasions. Alternatively, the rod-shaped plant virus carrier can be administered as a sustained release formulation, in which case less frequent administration is required. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

Pharmaceutical compositions can also include large, slowly metabolized macromolecules such as proteins, polysaccharides such as chitosan, polylactic acids, polyglycolic acids and copolymers (such as latex functionalized Sepharose™, agarose, cellulose, and the like), polymeric amino acids, amino acid copolymers, and lipid aggregates (such as oil droplets or liposomes).

For parenteral administration, compositions of the invention can be administered as injectable dosages of a solution or suspension of the substance in a physiologically acceptable diluent with a pharmaceutical carrier that can be a sterile liquid such as water oils, saline, glycerol, or ethanol. Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are preferred liquid carriers, particularly for injectable solutions.

The present invention is illustrated by the following examples. It is to be understood that the particular examples, materials, amounts, and procedures are to be interpreted broadly in accordance with the scope and spirit of the invention as set forth herein.

EXAMPLES

Example 1: Tobacco Mosaic Virus Rods and Spheres as Supramolecular High-Relaxivity MRI Contrast Agents To compensate for the low sensitivity of magnetic resonance imaging (MRI), nanoparticles have been developed to deliver high payloads of contrast agents to sites of disease. The inventors have developed supramolecular MRI contrast agents using the plant viral nanoparticle tobacco mosaic virus (TMV). Rod-shaped TMV nanoparticles measuring 300×18 nm were loaded with up to 3,500 or 2,000 chelated paramagnetic gadolinium (III) ions selectively at the interior (iGd-TMV) or exterior (eGd-TMV) surface, respectively. Spatial control is achieved through targeting either tyrosine or carboxylic acid side chains on the solvent exposed exterior or interior TMV surface. The ionic $T_1$ relaxivity per Gd ion (at 60 MHz) increases from 4.9 mM$^{-1}$s$^{-1}$ for free Gd(DOTA) to 18.4 mM$^{-1}$s$^{-1}$ for eGd-TMV and 10.7 mM$^{-1}$s$^{-1}$ for iGd-TMV. This equates to $T_1$ values of ~30,000 mM$^{-1}$s$^{-1}$ and ~35,000 mM$^{-1}$s$^{-1}$ per eGd-TMV and iGd-TMV nanoparticle. Further, the inventors show that interior-labeled TMV rods can undergo thermal transition to form 170 nm-sized spherical nanoparticles containing ~25,000 Gd chelates and a per particle relaxivity of almost 400,000 mM$^{-1}$s$^{-1}$ (15.2 mM$^{-1}$s$^{-1}$ per Gd). This work lays the foundation for the use of TMV as a contrast agent for MRI.

Experimental

TMV Propagation:

TMV was propagated in *N. benthamiana* plants. TMV was extracted in yields of 4.5 mg of virus per gram infected leaf material using established extraction methods. Boedtker, H, Simmons, N, JACS, 80, 2550-2556 (1958). Virus concentration in plant extracts was determined by UV-Vis absorbance ($\varepsilon_{260\ nm}$=3.0 mg$^{-1}$ mL cm$^{-1}$), and virus integrity was determined by size exclusion chromatography (SEC), and transmission and scanning electron microscopy (TEM and SEM) imaging.

TMV Bioconjugation:

To decorate the exterior TMV surface, the phenol ring of tyrosine underwent an electrophilic substitution (pH=9, 30 min.) with the diazonium salt generated from 3-ethynylaniline (25 molar equivalents (eq)) to incorporate a terminal alkyne. The resulting nanorods are designated eAlk-TMV. Bruckman et al., ChemBioChem 9, 519-523 (2008). Similarly, a terminal alkyne was incorporated onto the interior channel of TMV by targeting glutamic acid residues, designated iAlk-TMV. Wu et al., Journal of Materials Chemistry 21, 8550-8557 (2011). This was achieved by mixing propargyl amine (25 eq) with EDC (ethyldimethylpropyl-carbodiimide, 45 eq) and HOBt (n-hydroxybenzotriazole, 45 eq) for 24 hours. The HOBt is used to suppress EDC side product formation. Following sucrose gradient ultracentrifugation purification, the structural integrity of the particles was confirmed with TEM and SEC and the labeling efficiency was confirmed with MALDI-TOF MS.

Efficient conjugation of Gd(DOTA) azide to terminal alkyne labeled TMV (eAlk- and iAlk-TMV) is accomplished via a copper-catalyzed azide-alkyne cycloaddition (CuAAC) to form exterior or interior Gd conjugated TMV, designated eGd-TMV and iGd-TMV, respectively (FIG. 3). Initially, GdCl$_3$ was incubated with commercially available (azido-mono amide-1,4,7,10-tetraazacyclododecane-N,N', N'',N'''-tetraacetic acid; Macrocyclics) DOTA azide while maintaining a pH~6-7 (adjusted periodically with NaOH) over a six day-period to produce Gd(DOTA) azide. For both interior and exterior conjugation, the same protocol was used. Briefly, alkyne-labeled TMV (2 mg/ml) in 0.1 M potassium phosphate buffer pH 7.0 was mixed with Gd(DOTA) azide (5 eq to CP), aminoguanidine (2 mM), ascorbic acid (2 mM), and copper sulfate (1 mM) for 15 minutes. The reaction mix was purified using a 10-40% sucrose gradient and ultracentrifugation, and analyzed by TEM, SEM, SEC, and MALDI-TOF MS.

Thermal Transition to SNPs:

The standard protocol for thermal transition of native TMV rods to SNPs is heating of the sample at 0.1 mg/mL for 10 seconds at 96° C. with a Peltier thermal cycler. Alternatively, for iGd-TMV, PEG 8 kDa (0.5% w/v) was added to the reaction mix and incubation time was increased to 15 seconds.

MALDI-MS Analysis:

For MALDI-MS analysis, native and modified TMV (were denatured using guanidine hydrochloride (6 µL, 6 M) to the sample at 10-20 µg in 24 µL 0.1 M potassium phosphate buffer and mixing for 5 min at room temperature. Denatured proteins were spotted on MTP 384 massive target plate using Zip-Tips$_{\mu C18}$ (Millipore). MALDI-MS analysis was performed using a Bruker Ultra-Flex I TOF/TOF mass spectrometer.

Size Exclusion Chromatography (SEC):

All labeled particles were analyzed by SEC using a Superose6 column on the ÄKTA Explorer chromatography system (GE Healthcare). Samples (100 µg/100 µL) were analyzed at a flow rate of 0.5 mL/min using 0.1 M potassium phosphate buffer (pH 7.0).

Transmission Electron Microscopy (TEM):

Drops of TMV rods or SNPs in DI water were placed on copper TEM grids (5 µL, 0.1 mg/mL), allowed to adsorb for 5 minutes, washed with DI water, and negatively stained with 2% (w/v) uranyl acetate for 2 minute. Samples were examined using a Zeiss Libra® 200FE transmission electron microscope operated at 200 kV.

Gel Electrophoresis:

Denaturing gel electrophoresis was used to analyze protein subunits, specifically proteins were analyzed on denaturing 4-12% NuPAGE gels (Invitrogen) using 1×MOPS running buffer (Invitrogen) and 10 µg of sample. After separation, the gel was photographed using an Alphalmager (Biosciences) imaging system after staining with Coomassie Blue. ImageJ software was used for band analysis and to determine the protein concentration per SNP.

Scanning Electron Microscopy (SEM):

Samples were dried onto glass cover slips and then mounted on the surface of an aluminium pin stub with use of double-sided adhesive carbon discs (Agar Scientific). The stubs were then sputter-coated with gold in a high-resolution sputter coater (Agar Scientific, Ltd.) and transferred to a Hitachi 4500 scanning electron microscope.

ICP-OES Measurements:

The Gd per VNP ratio was determined using an ICP-OES (Perkin-Elmer ICP-OES 3300 DV) located in the Geology Department at Kent State University.

Relaxivity Measurements:

The ionic relaxivity of the engineered VNPs was tested using a pre-clinical 7.0T (300 MHz) MRI (Bruker BioSpec® 70/30USR), a clinical 1.5T (64 MHz) MRI (Siemens Espree), and a Bruker Minispec® mq60 relaxometer (60 MHz). A standard inversion recovery sequence protocol was used to determine the $T_1$ values on each of the instruments.

Results and Discussion

Spatially-Controlled Loading of MR Contrast Agents to the Exterior and Interior Surface of TMV.

Figure 2:
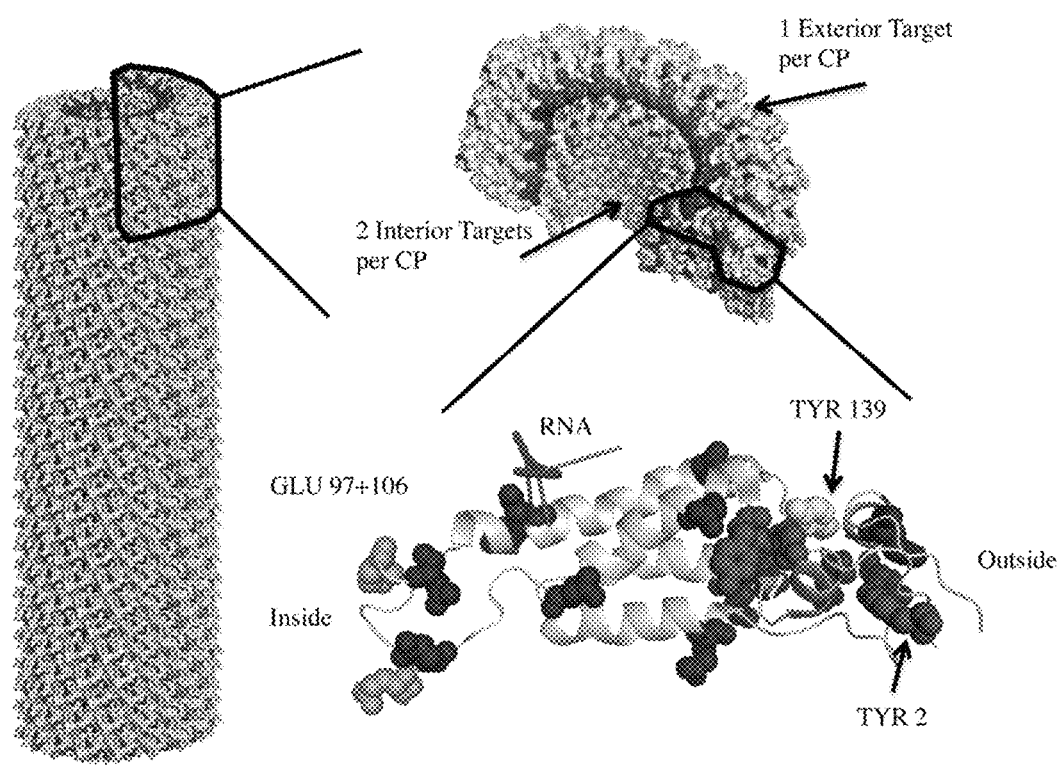
FIG. 2 provides a PyMol image of tobacco mosaic virus highlighting the interior glutamic acids, GLU97 and GLU106, exterior tyrosine, TYR139, for bioconjugation. Additional glutamic and aspartic acid residues and tyrosine residues are highlighted for reference.

TMV was propagated in *N. benthamiana* plants. Pure TMV nanorods were extracted in yields of 4.5 mg of virus per gram infected leaf material using established extraction methods. The exterior and interior surfaces of TMV's hollow rod can be efficiently functionalized using previously established bioconjugation protocols. FIG. 2 shows the high-resolution crystal structure of TMV highlighting carboxylic acids and tyrosine side chains (PDB ID 2TMV). Previous studies have indicated that exterior tyrosine 139 residues and interior glutamic acid 97 and 106 residues can be modified and functionalized using diazonium coupling or carbodiimide-based conjugation reactions.

The inventors explored both the exterior and interior surface for labeling with chelated gadolinium compounds. Using the interior surface provides the advantage that the exterior surface remains available for further tailoring with tissue-specific ligands. On the other hand, attaching the contrast agent to the exterior surface provides an opportunity to load the interior with drugs. To decorate the exterior TMV surface, tyrosine residues were targeted with the diazonium salt generated from 3-ethynylaniline to yield eAlk-TMV. Bruckman et al., ChemBioChem 9, 519-523 (2008). Similarly, a terminal alkyne was incorporated onto the interior channel of TMV by targeting glutamic acid residues, designated iAlk-TMV. Wu et al., Journal of Materials Chemistry 21, 8550-8557 (2011). Following sucrose gradient ultracentrifugation purification, the structural integrity of the particles was confirmed with TEM and SEC and the labeling efficiency was confirmed with MALDI-TOF MS.

Efficient conjugation of Gd(DOTA) azide to terminal alkyne labeled TMV (eAlk- and iAlk-TMV) was accomplished via a copper-catalyzed azide-alkyne cycloaddition (CuAAC) to form exterior or interior Gd conjugated TMV, designated eGd-TMV and iGd-TMV, respectively (FIG. 3). eGd-TMV and iGd-TMV formulations were purified using a 10-40% sucrose gradient and ultracentrifugation. This reaction gave an overall yield of 50-60% i/eGd-TMV, as confirmed by UV-Vis absorption to measure the TMV concentration ($AbS_{260\,nm}$=3 for 1 mg/ml) and SDS-PAGE. The structural integrity of the modified TMV particles was confirmed with sucrose gradients (matching light scattering region to native TMV), SEC, and TEM. A representative TEM image of iGd-TMV is shown in FIG. 4B. The successful incorporation of Gd-DOTA-azide onto the interior or exterior surfaces of TMV was confirmed using MALDI-TOF MS (FIGS. 3C and 3D) and ICP-OES (see Table 1).

TABLE 1

Longitudinal relaxivity values for Gd-TMV particles.

| VNP | Gd/VNP | Relaxivity per Gd (and per particle) mM$^{-1}$s$^{-1}$ | | |
|---|---|---|---|---|
| | | 60 MHz | 64 MHz | 300 MHz |
| eGd-TMV | 1,712 | 18.4 (31,501) | 15.7 (26,896) | 6.7 (11,402) |
| iGd-TMV | 3,417 | 10.7 (36,562) | 11.0 (37,519) | 4.7 (15,932) |
| iGd-SNP | 25,815 | 15.2 (392,388) | 13.2 (340,758) | 3.7 (95,515) |
| Gd(DOTA) | 1 | 4.9 | 4.9 | 4.9 |

For eGd-TMV, the mass spectrum (MS) shown in FIG. 3C displays peaks attributed to eAlk-TMV/wt-TMV coat proteins (CP) (eAlk, 17713 m/z), CPs with one (1-Gd, 18339 m/z) and two (2-Gd, 19094 m/z) Gd(DOTA) molecules attached. Similarly, the MS of iGd-TMV shown in FIG. 3D displays peaks attributed to iAlk-TMV/wt-TMV CPs (iAlk, 17618 m/z), CPs with one (1-Gd, 18359 m/z), two (2-Gd, 19044 m/z), and three (3-Gd, 19671 m/z) Gd(DOTA) molecules attached. The differences in mass values obtained are attributed to the DOTA molecule only, indicating that the chelated Gd ions did not remain chelated to DOTA after ionization. It should be noted that the presence of Gd was confirmed using ICP-OES.

Interestingly, MALDI-TOF MS characterizations of both the exterior and interior labeling indicate one additional amino acid modification per CP than previously reported. Schlick et al., JACS 127, 3718-3723 (2005). For exterior conjugation, the MS indicates a majority of the CPs that make up eGd-TMV have one Gd(DOTA), likely attached to TYR139, a small amount of CPs that are un-labeled, and a small amount of CPs that contain two Gd(DOTA) molecules per CP. Of the four tyrosine residues contained in the TMV coat protein, TYR139, TYR2, TYR70, and TYR72 (see FIG. 2), only Tyr139 has proven to be the primary reactive tyrosine. Based on the crystal structure it appears that TYR2 is solvent-exposed (more than TYR70 and TYR72), and the inventors believe that TYR2 is the potential second attachment site (see FIG. 2). For interior labeling, glutamic acids GLU97 and GLU106 have been proven to undergo bioconjugation while the third modification site remains unclear. The TMV coat protein includes several aspartic and glutamic acids that could serve as potential attachment sites (highlighted in blue in FIG. 2).

Quantitative labeling of TMV's interior and exterior surface with Gd was confirmed using ICP-OES. Data indicate that the exterior (eGd-TMV) was loaded with 1,712 Gd per particle and the interior (iGd-TMV) was loaded with 3,417 Gd per particle. The ICP-OES results are in agreement with the MALDI-TOF MS results. The results are exciting at least in part because previous studies have not indicated labeling of a second tyrosine or third carboxylic acid.

Thermal Transition of Contrast Agent Loaded TMV Rods into SNPs

In view the capability of TMV to form uniform SNPs (FIG. 4A), the inventors explored the thermal transition of chemically modified TMV particles (FIG. 4). Bruckman et al., J Mater Chem B Mater Biol Med. Mar. 14; 1, 1482-1490 (2013). Initially, the exterior modified TMV particles (eGd-TMV) were tested. It was found that no SNPs were formed after heating for 10 seconds at 96° C. (FIG. 4C). The conditions were expanded to extended incubation times (up to 30 seconds) and addition of additives such as PEG, urea, guanidinium chloride, triton X-100 and at high and low ionic strengths and found that no SNPs were formed. Finally, the inventors attempted to form SNPs with eAlk-TMV, thinking the DOTA group was too large and blocking the assembly. Again the SNPs did not form and only broken protein aggregates were found. This may suggest that TYR139 might play a role in the formation and stability of SNPs.

Subsequently, the thermal transition of interior modified TMV (iGd-TMV) to SNPs was tested. Using the standard protocol, i.e. heating for 10 seconds at 96° C. with a Peltier thermal cycler, formation of SNPs was not noticeable. While a lack of rod-shaped particles indicated that TMV was denatured, only irregular protein aggregates were observed. Similarly, a variety of additives were used to either increase or decrease TMVs stability (listed above). It was found that addition of PEG 8 kDa (0.5% w/v) to the reaction mix improved the stability of SNPs and decrease non-specific protein aggregation. After heating for 10 seconds, more regular SNP formation was found, however, the transition was incomplete, meaning that many rod-shaped TMV particles were still detectable in the sample (FIG. 4D). The rods appeared to be feeding into the SNPs indicating an end-in feeding/melting mechanism. Next, the incubation time was increased from 10 to 15 seconds and found that all of the rods were transitioned to SNPs, as seen with TEM (FIG. 4E) and SEM (FIG. 4F). A longer heating time is required to fully transition iGd-TMV into iGd-SNPs compared to native TMV. The inventors propose that the requirement of additional incubation time is because the interior modified TMV are more stable than native TMV. More stable interior modified TMV particles were confirmed using a differential scanning calorimeter. Native TMV was found to fall apart at 65° C., whereas iAlk-TMV remained stable until a temperature of 80° C. was reached. Modification of glutamic acids 97 and 106 has been shown to decrease the electrostatic repulsion between CPs, therefore leading to stronger attraction between CPs. Lu et al., Virology 225, 11-20 (1996).

Analysis of the SNP size distribution was done using TEM (FIG. 4E), SEM (FIG. 4F) and dynamic light scattering (DLS) with a Nanosight size analyzer (FIG. 4G) and a standard DLS instrument (Brookhaven). It was found that there is some variability from experiment to experiment with the size of the SNP batches varying between 150 nm to 200 nm. Within a particular batch, however, there is a narrow size distribution. The SNP batch utilized for the described studies, measured a hydrodynamic radius of 170±41 nm in diameter as determined by Nanosight (FIG. 4G) and DLS. This is in agreement with TEM and SEM measurements that indicated a SNP size of 152 nm±58 nm (the smaller size is explained that in SEM and TEM dried samples are measured whereas Nanosight and DLS record the hydrodynamic radii).

The Gd loading per SNP was determined using a combination of ICP-OES for Gd concentration and SDS-PAGE for protein concentration. Here, when it is assumed that the coat proteins form densely packed SNPs upon thermal transition, a 170 nm-sized SNP would contain ~75,400 coat proteins (35.4 times the number of coat protein found in a single TMV rod). The protein concentration was estimated using SDS-PAGE protein gel electrophoresis followed by Coomassie staining and band analysis using ImageJ software. Based on the SDS-PAGE and size analysis, the inventors estimated that a 1 mg/ml solution of SNPs contained $4.73 \times 10^{11}$ particles/mL, or a molar concentration of $7.05 \times 10^{-10}$ M. ICP-OES analysis of the same 1 mg/ml solution of SNPs contained 2.85 ppm Gd, or $1.82 \times 10^{-5}$ M, yielding SNPs with 25,815 Gd per SNP (see Table 1).

Figure 5:
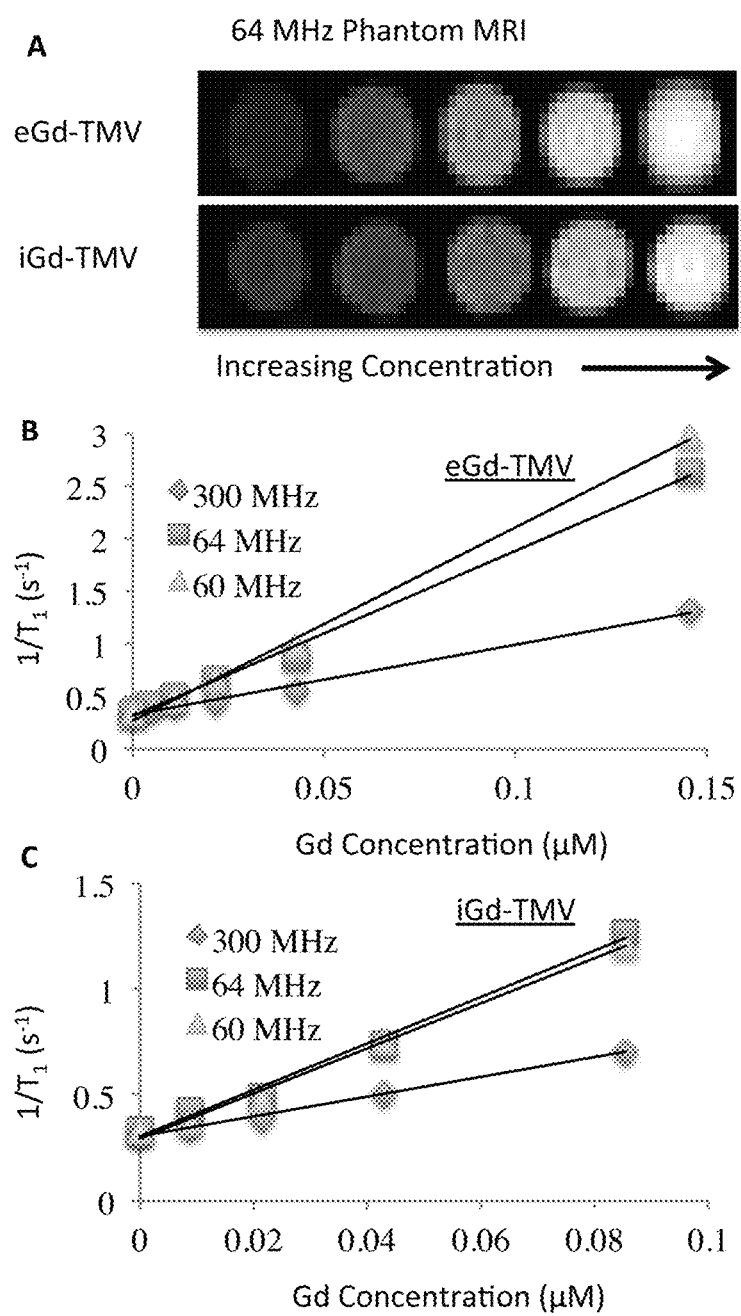
FIG. 5 provides (A) phantom images of tubes containing eGd-TMV, iGd-TMV and Gd(DOTA) with the corresponding Gd concentrations in M; measured using a clinical 1.5T MRI. Plot of 1/T$_1$ versus Gd concentration (mM) for eGd-TMV (B) and iGd-TMV (C) taken from three MR sources. The slopes of the plots correspond to the ionic relaxivity. Data were collected at varying field strengths (300 MHz, 64 MHz, and 60 MHz).

The ionic relaxivity of the engineered VNPs was tested using a pre-clinical 7.0T (300 MHz) MRI (Bruker BioSpec® 70/30USR), a clinical 1.5T (64 MHz) MRI (Siemens Espree), and a Bruker Minispec® mq60 relaxometer (60 MHz). A standard inversion recovery sequence protocol was used to determine the $T_1$ values on each of the instruments. Shown in FIG. 5A is the inversion recovery image ($T_1$=2000 ms) of iGd-TMV and eGd-TMV phantoms taken on the clinical MRI (64 MHz, 1.5T). The concentrations increase from left to right with the phantom on far left being water. In order to determine the ionic relaxivities of Gd, $1/T_1$ (units=1/seconds) was plotted against the concentration of Gd (in µM) for each formulation and field strength; the slope of each correlation line is the ionic relaxivity ($r_1$, see FIG. 5B+C). The relaxivity of the entire particle was computed by multiplying the ionic relaxivity by the number Gd ions per particle determined by ICP-OES. Similar analysis was performed on the Gd-SNPs (data are summarized in Table 1). Next, ionic relaxivity values were determined using a preclinical MRI and relaxometer with a similar inversion recovery sequence (see Table 1). The ionic relaxivity increased at lower field strengths. Caravan et al., Contrast Media & Molecular Imaging 4, 89-100 (2009).

As with other macromolecular carriers, the relaxivity of DOTA chelated Gd ions was found to increase after conjugation to TMV, compared to free Gd(DOTA) in solution. The increase in ionic relaxivity is greater for exterior labeling of TMV compared to the interior labeling, 18.4 mM$^{-1}$s$^{-1}$ and 10.7 mM$^{-1}$s$^{-1}$, respectively. This is primarily attributed to the difference in molecular attachment site. Exterior modification is carried out targeting tyrosine side chains and interior loading is accomplished through modification of glutamic acids. The ring structure of the tyrosine side chain induces rigidity, whereas the alkyl chain in the glutamic acids is comparatively flexible. The more rigid the attachment site, the higher the enhancement in relaxivity. This is consistent with previous reports that showed that amino acid stiffness lowers the tumbling rate thus increasing relaxivity. For example, exterior lysine residues of MS2 were labeled with bis(HOPO) ligands to chelate Gd, they exhibited an ionic $T_1$ relaxivity of 23.2 mM$^{-1}$s$^{-1}$, while interior tyrosine residues labeled with the same bis(HOPO) ligand demonstrated an ionic $T_1$ relaxivity of 31.0 mM$^{-1}$s$^{-1}$ (at 60 MHz). Hooker et al., Nano Letters 7, 2207-2210 (2007).

Additionally, after transition of iGd-TMV to SNPs, the ionic relaxivity increases from 10.7 mM$^{-1}$s$^{-1}$ to 15.2 mM$^{-1}$s$^{-1}$ at 60 MHz. One potential explanation for the increase is because after transition to SNPs, the overall mobility (correlated to the tumbling rate) of each Gd may be lowered because of molecular crowding from the dense packing of proteins into spheres. Here, it is important to note the drastic difference in per nanoparticle relaxivity between TMV rods and spheres. Based on ICP results, the iGd-TMV particles have 3,417 Gd atoms per rod, which gives a per particle relaxivity of 36,562 mM$^{-1}$s$^{-1}$, while the Gd-SNPs contain 25,815 Gd atoms per sphere giving a per particle relaxivity of 392,388 mM$^{-1}$s$^{-1}$.

Figure 6:
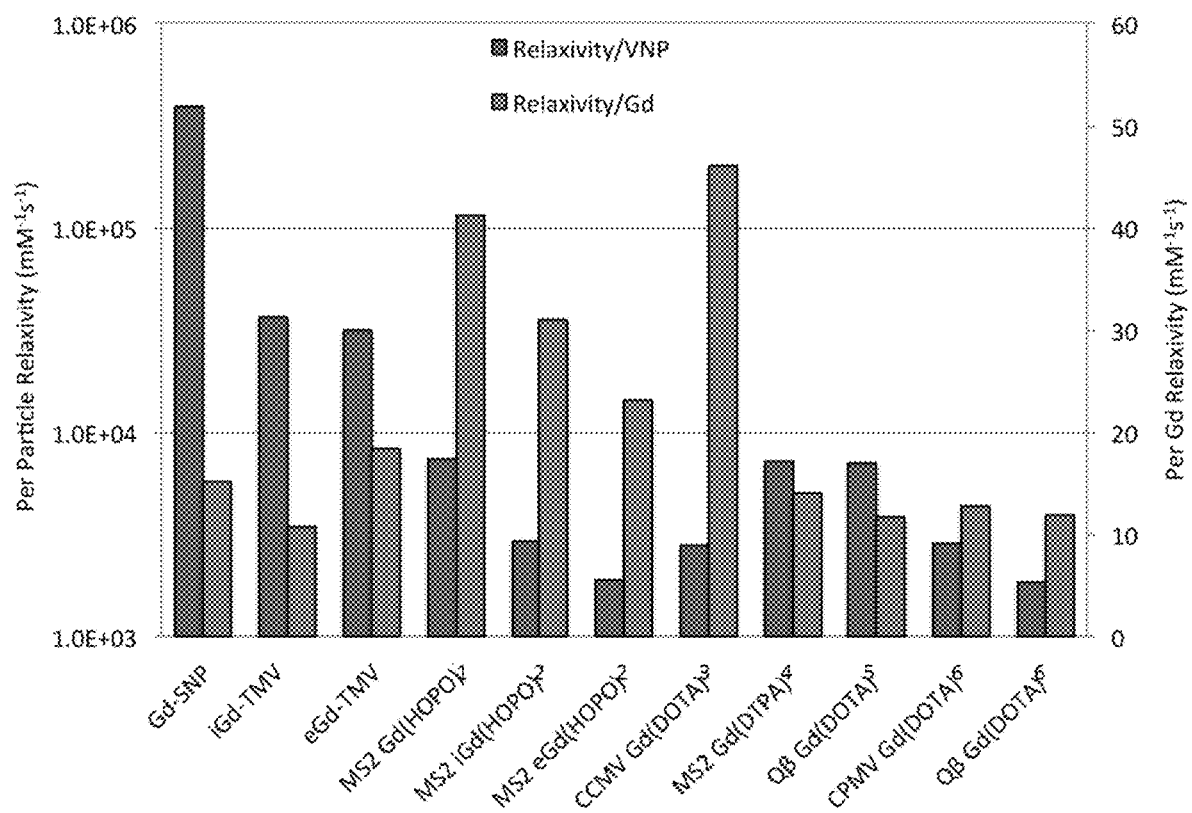
FIG. 6 provides a graph comparing the nanoparticle relaxivities (left axis) and ionic relaxivities (right axis) of TMV particles described in Example 1 against other Gd-VNPs at 60 MHz (refs 1, 2, or 5) or 64 MHz (refs 3, 4, and 6). The cited references are: #1 Garimella et al., JACS, 133, 14704-14709 (2011); #2 Hooker et al., Nano Letters 7, 2207-2210 (2007); #3 Liepold et al., Magn Reson Med 58, 871-879 (2007); #4 Anderson et al., Nano Letters 6, 1160-1164 (2006); #5 Pokorski et al., JACS 133, 9242-9245 (2011); #6 Prasuhn et al., Chemical Communications 28, 1269-71 (2007).

Based on their biocompatibility, monodispersity and ability to undergo multiple rounds of site-selective chemical and/or genetic modification, several icosahedral VNPs have previously been utilized as scaffolds for the presentation of MRI contrast agents, these include cowpea chlorotic mottle virus (CCMV), cowpea mosaic virus (CPMV), and bacteriophages MS2 and Qβ. In all cases enhancements of ionic T1 relaxivities above FDA-approved Magnevist® (data are summarized in FIG. 6). The Gd-TMV particles generated in this study show similar T1 relaxivity enhancements to VNPs decorated with Gd chelated with DOTA or DTPA ligands, see FIG. 6. While the ionic relaxivity of TMV is comparable to other magnetic VNPs, the rod-shaped Gd loaded TMV particles have a four times higher per particle relaxivity (of more than 30,000 mM$^{-1}$s$^{-1}$) compared to icosahedral VNPs (see FIG. 6). These results are exciting and expected because while the size of TMV is bigger (volume=7.6×10$^4$ nm$^3$ of TMV vs 1.4×10$^4$ nm$^3$ for a 30 nm-sized icosahedron), the relaxivity per volume ratio (R1/V) is similar. The R1/V for eGd-TMV and iGd-TMV is 0.41 and 0.48, respectively, while the R1/V for the spherical VNPs ranges from 0.13 to 0.52. To date the highest per Gd relaxivities were reported by the Francis Lab, who utilized a special HOPO ligand. Raymond et al., Bioconjugate Chemistry 16, 3-8 (2005).

Finally, the enhancement in ionic relaxivity per Gd is maintained after thermal transition to SNPs. Phantom MRI tests indicate that the relaxivity is even further enhanced. The per particle relaxivity of the SNPs (4×10 mM$^{-1}$s$^{-1}$) bridges the gap between contemporary VNPs (T1 relaxivity near 10$^4$ mM$^{-1}$s$^{-1}$) and dendrimers, silica nanoparticles and perfluorocarbons, which have per particle T1 relaxivities in the 10$^6$ mM$^{-1}$s$^{-1}$ range.

Conclusion

In conclusion, the inventors have developed a plant viral-based nanoparticle platform suitable for application as an imaging agent. Covalent attachment of chelated gadolinium ions to the supramolecular carrier leads to enhanced ionic relaxivity of the Gd ions based on reduced tumbling rates. Multivalent display leads to relaxivity per nanoparticle four times higher than over VNP contrast agents. Furthermore, the transition of rod-shaped TMV to SNPs improved the ionic T1 relaxivity per Gd based on molecular crowding, while further increasing the loading of Gd per particle yielding a protein based MRI contrast agent with a T1 relaxivity of 400,000 mM$^{-1}$s$^{-1}$. The Gd-loaded TMV rods and spheres reach T1 relaxivities comparable to state-of-the-art dendrimers.

Example 2: Dual-Modal MRI and Fluorescence Imaging of Atherosclerotic Plaques In Vivo Using VCAM Targeted Tobacco Mosaic Virus The nanoparticles formed by plant viruses are emerging tools for molecular imaging in medicine. Here, the rod-shaped tobacco mosaic virus was used to target and image atherosclerotic plaques in vivo. TMV was loaded with magnetic resonance (MR) and fluorescence contrast agents to provide a dual-modal imaging platform. Targeting to atherosclerotic plaques was achieved with vascular cell adhesion molecule (VCAM) receptors present on activated endothelial cells. Dual, molecular imaging was confirmed using a mouse model of atherosclerosis.

Methods

Isolation of TMV. TMV particles were isolated from *Nicotiana benthamiana* or *N. rusitca* plants using a previously established protocol. Boedtker H, Simmons N S. JACS, 80:2550-6 (1958). The TMV concentration was determined based on UV-Vis absorbance at 260 nm with an extinction coefficient of 3.0 mL mg$^{-1}$ cm$^{-1}$.

Bioconjugation of TMV particles. A peptide was chosen to target vascular cell adhesion molecule (VCAM-1) receptors on the surface of activated endothelial cells. Nahrendorf et al., Circulation. 114:1504-11 (2006) The VCAM-1 targeting peptide labeled with an azide group was synthesized using standard peptide synthesis techniques. Targeted (VCAM-TMV) and non-targeted (PEG-TMV) rods were synthesized using the following sequence of established reactions. Bruckman et al., J Mater Chem B Mater Biol Med. 1:1482-90 (2013). First, the exterior was labeled with a terminal alkyne by targeting tyrosine 139 residues. Azido PEG or VCAM was attached to the exterior alkyne using a copper-catalyzed azide-alkyne cycloaddition (CuAAC) reaction. Next, the interior was labeled with terminal alkynes by targeting glutamic acids 97 and 106 with a primary amine and EDC. Finally, MRI contrast agents (Gd(DOTA) azide) and fluorescent molecules (sulfo-Cy5 azide) were attached to TMV using the CuAAC reaction. Modified TMV particles were characterized for labeling efficiency, structural integrity, and magnetic $T_1$ relaxivity enhancement. Labeling efficiency was confirmed using MALDI-TOF mass spectrometry, SDS-PAGE electrophoresis, ICP-OES (for Gd), and UV-Vis absorbance (for Cy5). Particle integrity was confirmed by TEM and SEC. The ionic relaxivity of engineered Gd-loaded TMV particles was tested using a Bruker Minispec® mq60 relaxometer.

MALDI-MS analysis. For MALDI-MS analysis, native and modified TMV were denatured using guanidine hydrochloride (6 μL, 6 M) to the sample at 10-20 μg in 24 μL 0.1 M potassium phosphate buffer and mixing for 5 min at room temperature. Denatured proteins were spotted on MTP 384 massive target plate using Zip-Tips$_{\mu C18}$ (Millipore). MALDI-MS analysis was performed using a Bruker Ultra-Flex I TOF/TOF mass spectrometer.

Size exclusion chromatography (SEC). All labeled particles were analyzed by SEC using a Superose6 column on the ÄKTA Explorer chromatography system (GE Healthcare). Samples (100 μg/100 μL) were analyzed at a flow rate of 0.5 mL/min using 0.1 M potassium phosphate buffer (pH 7.0).

Transmission electron microscopy (TEM). Drops of TMV formulations in DI water were placed on copper TEM grids (5 μL, 0.1 mg/mL), allowed to adsorb for 5 minutes, washed with DI water, and negatively stained with 2% (w/v) uranyl acetate for 2 minute. Samples were examined using a Zeiss Libra® 200FE transmission electron microscope operated at 200 kV.

Gel electrophoresis. Denaturing gel electrophoresis was used to analyze protein subunits, specifically proteins were analyzed on denaturing 4-12% NuPAGE gels (Invitrogen) using 1×MOPS running buffer (Invitrogen) and 10 μg of sample. After separation, the gel was photographed using an AlphaImager (Biosciences) imaging system after staining with Coomassie Blue. ImageJ software was used for band analysis and to determine the degree of labeling with PEG and VCAM.

Relaxivity measurements. The ionic relaxivity of the Gd(DOTA)-modified TMV was tested using a Bruker Minispec mq60 relaxometer (60 MHz). The Gd concentration was determined using an ICP-OES. Multiple concentrations of TMV were used with a standard inversion recovery sequence protocol to determine the $T_1$ values.

Animal protocols. All experiments were carried out using IACUC approved procedures. ApoE$^{-/-}$ mice were used for all experiments. ApoE$^{-/-}$ mice had an average age of 22 weeks were fed a western diet (1.25% cholesterol, 20% fat, Research Diets Inc.) for 14-18 weeks were injected via the tail vein with virus particles at an amount of 10 mg/kg. Healthy C57BL/6 mice of the same age served as negative controls.

Ex vivo fluorescence imaging. Mice were euthanized and dissected to remove aortas 3 hours post administration of TMV and respective controls. The aorta was then fixed in 4% (v/v) paraformaldehyde in 30% (v/v) sucrose overnight at 4° C. After fixation, the aorta was cleaned to remove fatty connective tissue. The cleaned aorta was then imaged using a Maestro fluorescence imaging system to detect Cy5 fluorescence signal. Image cubes were obtained with an exposure time of 800 ms per step. The obtained image cubes were background subtracted prior to quantitative image analysis.

Immunofluorescence Imaging. Immediately after ex vivo fluorescence imaging, the cleaned aortas were cut into 10-12 2-4 mm long sections and embedded in OCT and flash frozen. The frozen samples were cryosectioned to 10 m sections and mounted on Fisherbrand ColorFrost Plus microscope glass slides for staining. Freshly sectioned aortas were stained for macrophage cell marker CD68 (BioLegend) and mounted using mounting media containing DAPI (Fluoroshield with DAPI, Sigma).

MRI analysis. In vivo MRI scans were performed using a Bruker BioSpin® 7.0T 70/30USR MRI system. This system has been outfitted with an RF mouse coil. Mice were anesthetized for all procedures (isoflurane 1.5%; $O_2$ 2.5 L/min) and their respiration, body temperature, and heart rate (ECG) were monitored real-time. Following multiple scouting scans, a $T_1$-weighted Multi Slice Multi Echo (MSME) black-blood fat-suppression sequence was optimized to detect the aorta wall with the following parameters: TR/TE=600/8.0 ms, 8 axial slices 1 mm thickness with 1.5 mm slice separation, two averages, matrix=256×256, field of view=2.98 cm, acquisition time=10:14 minutes. Respiration and ECG triggering was applied per slice. Images were taken prior and post TMV administration, formulations were injected while the animal remained in the MRI machine. Sequential scans were performed for up to 150 minutes. Statistical analysis of MRI results was performed using MatLab program to determine the contrast to noise ratio (CNR).

Results

Figure 7:
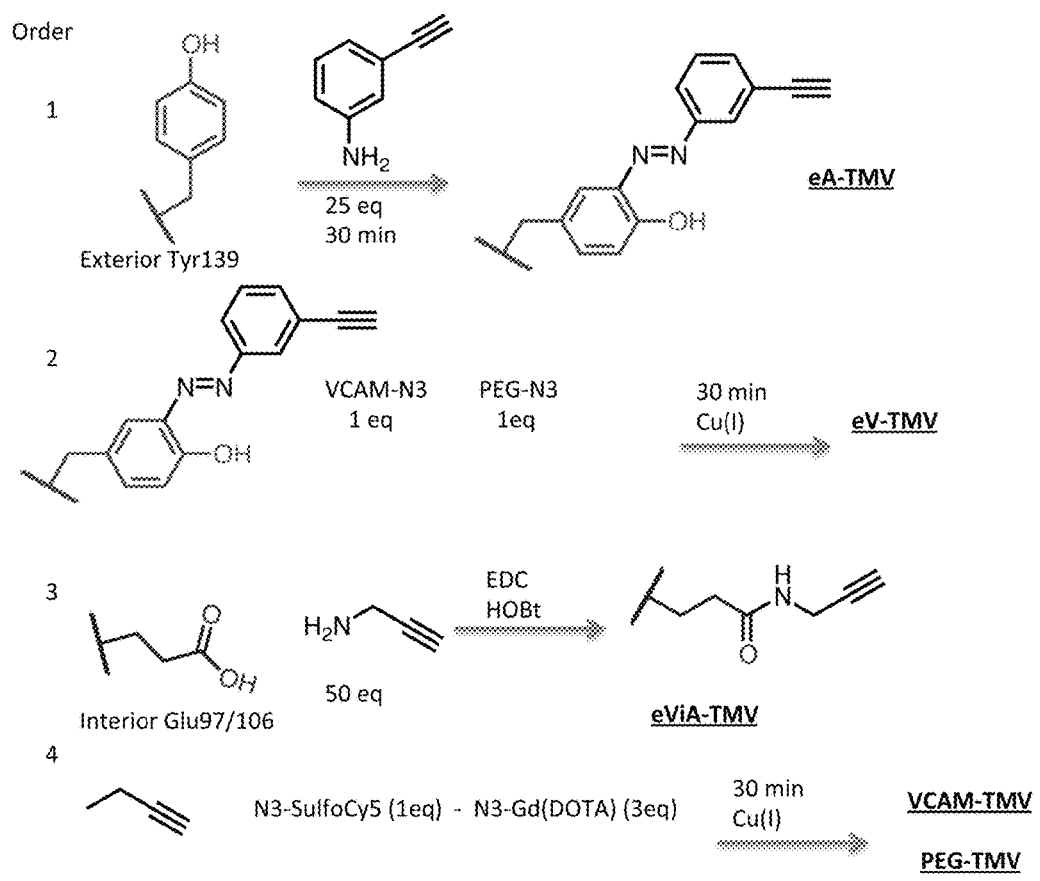
FIG. 7 provides a reaction scheme showing the bioconjugation sequence used to engineer TMV particles and data table showing labeling efficiencies of TMV with Cy5 optical dye, Gd(DOTA) MR contrast agent, the T1 relaxivity at 60 MHz in mM$^{-1}$s$^{-1}$, and the number of VCAM (targeting ligand, also includes PEG) and PEG only (negative control) per TMV.
Figure 8:
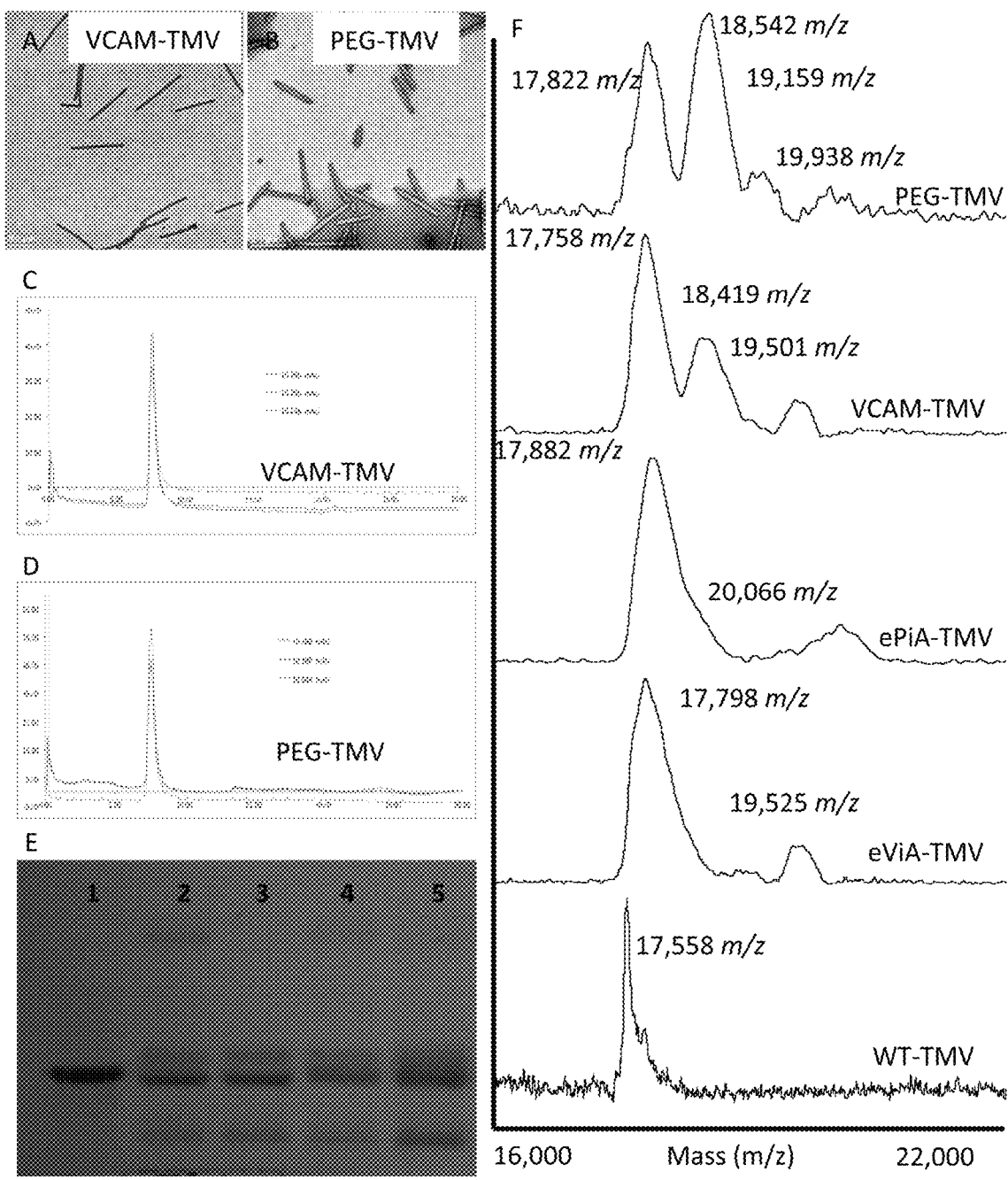
FIG. 8 provides graphs and images based on characterization of VCAM-TMV and PEG-TMV by TEM imaging after UAc staining (A, B), size exclusion chromatography (C, D), SDS-PAGE (E) and MALDI-TOF mass spectra (F). SDS-PAGE lane assignments are: 1-Wt-TMV, 2-eViA-TMV, 3-ePiA-TMV, 4-VCAM-TMV (after labeling with Cy5 and Gd(DOTA)), 5-PEG-TMV (after labeling with Cy5 and Gd(DOTA)).
Figure 9:
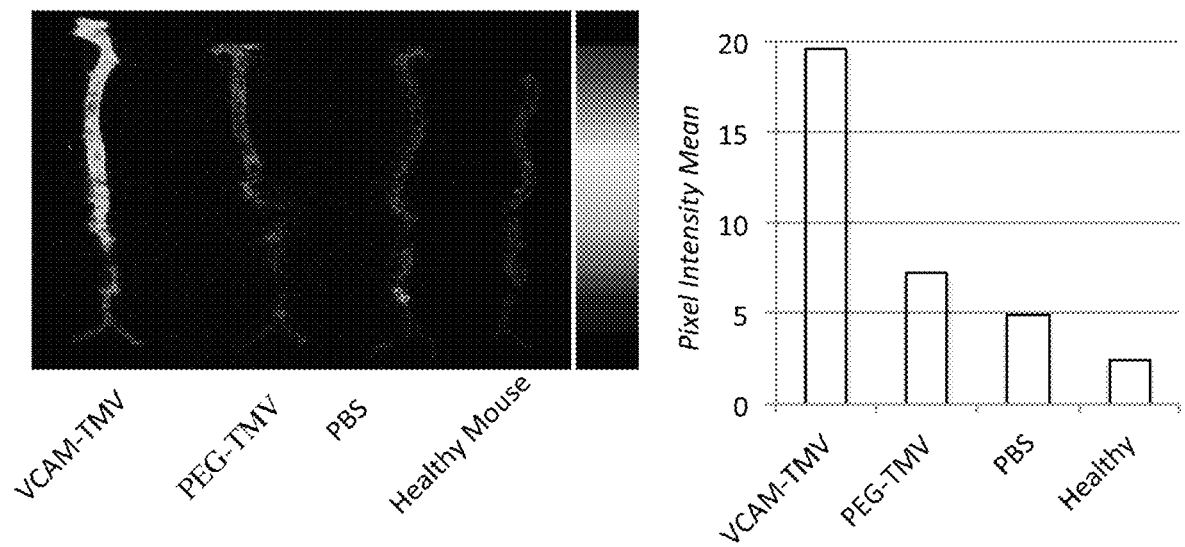
FIG. 9 provides ex vivo optical imaging of aortas from ApoE$^{-/-}$ mice after administration of targeted TMV sensors and respective control and a bar graph showing pixel intensity mean after quantitative image analysis using Maestro Imager software.

Bioconjugation to synthesize VCAM-TMV and PEG-TMV. TMV particles were modified with contrast agents, PEG and targeting ligands to target VCAM-1 receptors that are overexpressed on endothelial cells in areas of atherosclerotic plaque development (FIG. 7). The inventors chose known VCAM-1 ligand: VHPKQHR. VCAM-1 peptide and PEG were synthesized to incorporate a linker with an azide functional group for conjugation to TMV using CuAAC chemistry. A PEG$_{2000}$ labeled TMV was synthesized as a non-targeting nanoparticle control. The specific sequence for modifying TMV is outlined in FIG. 7. In brief, first the exterior surface is modified with alkyne ligation handles followed by modification with PEG and VCAM peptide. Second, the interior is modified with alkyne ligation handles followed by modification with optical and MR contrast agents (Cy and Gd(DOTA)). TEM imaging and SEC analysis indicate that the particles remain structurally sound; further SEC indicates covalent modification with Cy5 (as indicated by co-elution of the dye-specific peak at 650 nm with the protein peak at 260 nm, see FIG. 8). A combination of SDS-PAGE, MALDI-TOF, UV-Vis, and ICP-OES measurements were performed to determine the degree of labeling: MADLI-TOF results are in good agreement with sequential modification of the TMV coat proteins. Further, based on SDS-PAGE lane analysis (FIG. 8, ImageJ), the inventors estimate coverage with ~500 VCAM peptides and PEG per VCAM-TMV and PEG-TMV, respectively, which corresponds to 25% of the coat proteins being labeled (TMV consists of 2130 identical coat protein units). UV-Vis was used to determine the degree of Cy5 labeling and ICP-OES was used to determine the number of incorporated Gd(DOTA). It was found that VCAM-TMV and PEG-TMV were labeled with ~460 and ~510 Cy5 dyes, respectively, thus also covering 25% of the available coat proteins. The degree of labeling was significantly higher—a desired results, because the higher the density of the chelated Gd(DOTA) ions, the higher the $T_1$ relaxivity per nanoparticle; VCAM-TMV was loaded with ~1,200 chelated Gd ions, resulting in a per particle relaxivity of 17,567 mM$^{-1}$s$^{-1}$ at 60 MHz. (FIG. 9).

VCAM-TMV targeting was confirmed using ex vivo fluorescence imaging of aortas. ApoE$^{-/-}$ mice were able to develop sufficient plaque coverage in 14-18 weeks on a high fat/cholesterol diet (based on post histological analysis). Along with VCAM-TMV (n=4) for the targeting contrast agent and PEG-TMV (n=3) as the negative nanoparticle control, PBS (n=3) and free contrast agent (sulfo-Cy5-azide and Gd(DOTA)-azide) (n=1) were injected at concentrations matching the TMV labeled injection dose. Finally, VCAM-TMV was injected into the age-matched healthy mouse model C57BL/6 (n=1) to demonstrate that VCAM-TMV particles do not accumulate at healthy endothelial cells and arteries. Data indicate selective targeting and accumulation of TMV-VCAM in aortas from ApoE$^{-/-}$ fed on a high western diet. Fluorescence intensity from aortas from animals injected with VCAM-TMV (fluorescence intensity (FI)=19.6) was significantly higher than signals obtained from PEG-TMV (FI=7.2), PBS (FI=4.9), and the aorta from a C57BL/6 mouse (FI=2.4).

Immunofluorescense imaging of cryo-sectioned aortas further confirmed VCAM-TMV targeting and accumulation in areas of atherosclerotic plaque. Cryosections of aortas were stained for macrophages (CD68 antibody) to confirm the presence of plaques. Images of an aorta section from mice injected with VCAM-TMV, PEG-TMV, and PBS were obtained. Each mouse aorta was quantitatively analyzed for the number of sections that contained plaques and that also contained fluorescent TMV signal and found that 70% of plaque sections from aortas injected with targeted VCAM-TMV particles (n=4) showed TMV accumulation, while only 18% of aorta sections that were positive for PEG-TMV signals. No TMV (Cy5) signal was detected in aorta sections that did not indicate any areas of plaque development, therefore indicating that TMV does no non-specifically adhere to the vessel wall. VCAM-TMV was localized at the surface of the plaque, indicating targeting of activated endothelial cells expressing VCAM. There was no indication that VCAM-TMV particles were taken up by macrophages and incorporated into plaques.

Figure 10:
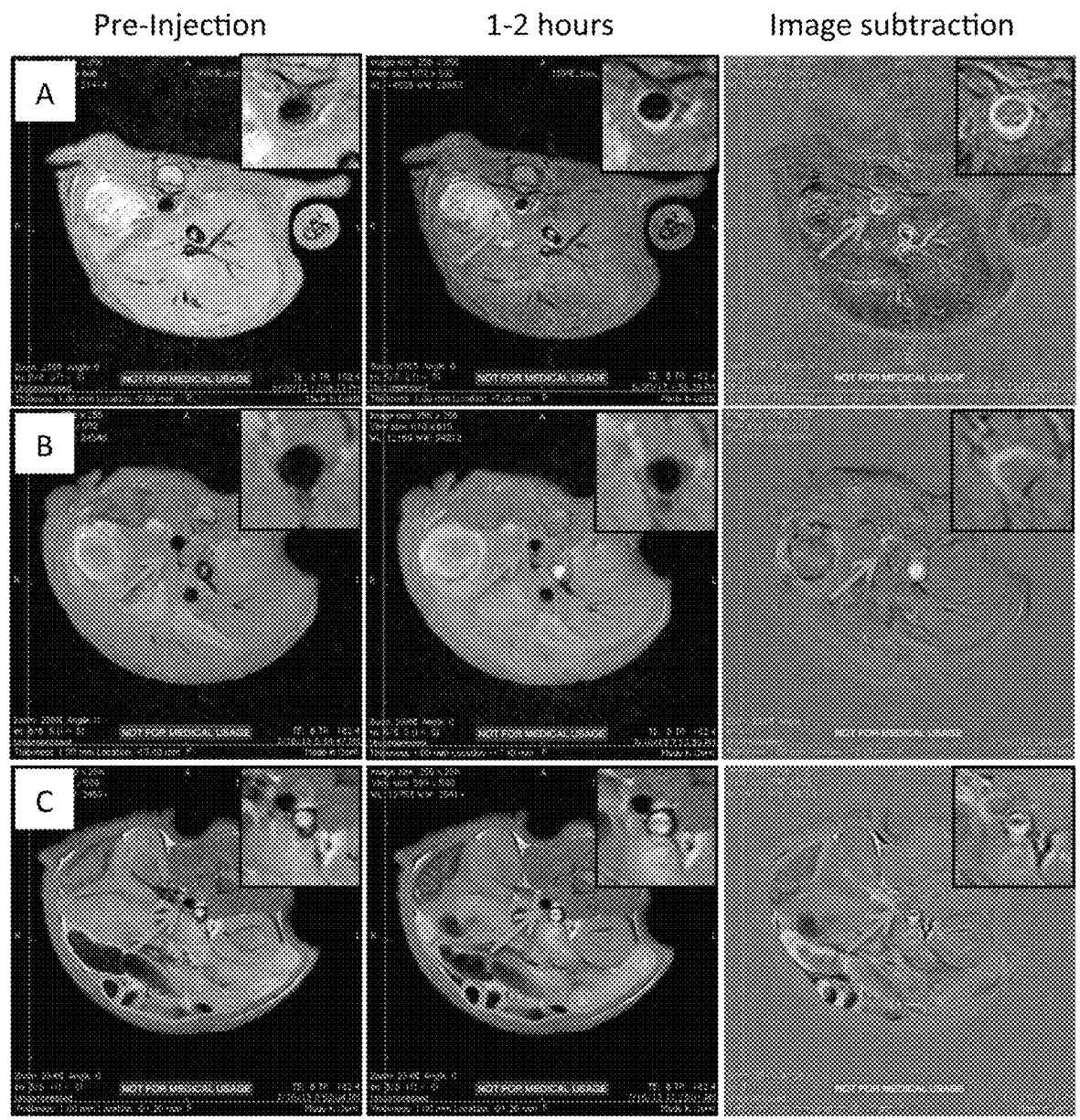
FIG. 10 provides images showing pre- and post-injection MRI scans of (A) VCAM-TMV, (B) Gd(DOTA), and (C) PBS. The third column is the subtracted image. Insets are magnified images of the abdominal aorta region of interest.

MR imaging atherosclerotic plaques in ApoE$^{-/-}$ mice using molecularly-targeted VCAM-TMV. MR imaging of ApoE$^{-/-}$ mice was conducted using the Gd(DOTA)-labeled VCAM-TMV sensors. Significant increase in contrast-to-noise (CNR) was observed in the vessel wall of the abdominal aorta (FIG. 10A). The increase in CNR increased over time and leveled off at around 60 minutes. Not all slices indicated accumulation of paramagnetic contrast agent, which is in agreement with not all slices containing plaques (this is also consistent with fluorescence analysis, see above). Free Gd(DOTA)) and PBS did not show any increase in CNR in the vessel wall (FIGS. 10B and C, respectively).

In summary, the data support the successful development of a molecularly-targeted TMV-based probe for dual MR and optical imaging of atherosclerotic plaques in mice.

The complete disclosure of all patents, patent applications, and publications, and electronically available materials cited herein are incorporated by reference. The foregoing detailed description and examples have been given for clarity of understanding only. No unnecessary limitations are to be understood therefrom. In particular, the inventors are not bound by theories described herein. The invention is not limited to the exact details shown and described, for variations obvious to one skilled in the art will be included within the invention defined by the claims.

What is claimed is:

1. A spherical nanoparticle imaging platform, comprising a spherical arrangement of the coat proteins of one or more rod-shaped plant virus particles linked to an imaging agent on an interior surface of the virus particle, formed by thermal transition of the rod-shaped virus particles, wherein the imaging platform has a longitudinal relaxivity of greater than about 10 mM$^{-1}$S$^{-1}$ per linked imaging agent when measured at 60 mHz at a physiological pH.

2. The spherical nanoparticle imaging platform of claim 1, wherein the rod-shaped plant virus is a tobacco mosaic virus.

3. The spherical nanoparticle imaging platform of claim 1, wherein the imaging agent is a chelated lanthanide.

4. The spherical nanoparticle imaging platform of claim 1, wherein the imaging platform has a longitudinal relaxivity of greater than about 15 mM$^{-1}$S$^{-1}$ per linked imaging agent when measured at 60 mHz at a physiological pH.

* * * * *